United States Patent [19]

Novotny et al.

[11] Patent Number: 5,631,374

[45] Date of Patent: May 20, 1997

[54] REAGENTS FOR DETECTION OF PRIMARY AMINES

[75] Inventors: Milos V. Novotny; Donald Wiesler; Jinping Liu, all of Bloomington, Ind.; You-Zung Hsieh, Taipei, Taiwan

[73] Assignee: Research Corporation Technologies, Inc., Tucson, Ariz.

[21] Appl. No.: 144,912

[22] Filed: Oct. 28, 1993

Related U.S. Application Data

[62] Division of Ser. No. 598,508, Oct. 16, 1990, Pat. No. 5,459,272.

[51] Int. Cl.$^6$ .......................... C07D 471/08; C07K 5/04; C07K 7/04; C08B 37/00; C07H 17/02

[52] U.S. Cl. .......................... 546/84; 544/333; 536/18.7; 536/27.1; 530/324; 530/326; 530/327; 530/330; 436/111; 436/86; 436/89; 436/128; 436/149; 436/150; 436/161

[58] Field of Search .................. 546/168, 84; 536/24, 536/18.7; 530/324, 326, 327, 330

[56] References Cited

U.S. PATENT DOCUMENTS

| | | | |
|---|---|---|---|
| 4,723,022 | 2/1988 | Givens et al. | 548/326 |
| 4,837,166 | 6/1989 | de Montigny et al. | 436/111 |
| 4,910,314 | 3/1990 | de Montigny et al. | 548/310 |

OTHER PUBLICATIONS

Beale et al. (1988) Fluorescence Reagents for High–Sensitivity Chromatographic Measurements of Primary Amines. *Anal. Chem.* 60: 1765–1769.

Beale et al. (1989) 3–Benzoyl–2– Quinolineacarboxaldehyde: A Novel Fluorogenic Reagent for the High–Sensitivity Chromatographic Analysis for Primary Amines. *Talanta* 36:321–325.

Beale et al. (1990) Application of 3–(2–Furoyl)Quinoline–2–Carbaldehyde as a Fluorogenic Reagents for the Analysis of Primary Amines by Liquid Chromatograpy with Laser–Induced Fluorescence Detection. *J. Chromatography* 499:579–587.

de Montigny et al. (1987) Naphthalene–2,3–dicarboxaldehyde/Cyanide Ion: A Rationally Designed Fluorogenic Reagent for Primary Amines., *Anal. Chem.* 59:1096–1101.

Gluckman, et al. (1984) Laser Fluorimetry for Capillary Column Liquid Chromatography: High–Sensitivity Detection of Derivatized Biological Compounds. *Journal of Chromatography* 317:443–453.

*Primary Examiner*—David B. Springer
*Attorney, Agent, or Firm*—Scully, Scott, Murphy & Presser

[57] ABSTRACT

The present invention is directed to derivatives of aroyl-2-quinoline-carboxaldehyde and their use in detection and quantification of minute amounts of primary amines.

15 Claims, 22 Drawing Sheets ially occurring and chemically synthesized molecules
REAGENTS FOR DETECTION OF PRIMARY AMINES This is a divisional of application Ser. No. 598,508, filed on Oct. 16, 1990 now U.S. Pat. No. 5,459,272.

FIELD OF THE INVENTION

The present invention is directed towards a method of ultrasensitive detection and quantification of primary amines by reaction of the primary amine with substituted aroyl-2-quinoline-carboxaldehyde (XArQCA) reagents, followed by measurement of the fluorescent product. Primary amines which may be detected by the present reagents include naturally occurring and chemically synthesized molecules such as alkyl amines, amino acids, peptides, proteins, glycoproteins, amino sugars and pharmaceuticals, as well as molecules into which a primary amine may be easily incorporated, such as reducing sugars, oligosaccharides and polysaccharides. The XArQCA reagents of the present invention are particularly useful because they are not fluorescent but, when reacted with a primary amine, a fluorescent isoindole product is generated that may be detected in minute amounts as low as $10^{-19}$ moles. This is several orders of magnitude more sensitive than most current detection systems provide. Furthermore, the substitutions on the XArQCA reagents represent a surprising improvement over known reagents since they promote formation of product from relatively hydrophilic reactants such as peptides, proteins and carbohydrates. The substituents of the present XArQCA reagents also facilitate separation of the isoindole product, allowing reaction of complex mixtures of primary amines with the present reagents, followed by separation of individual components, before detection and quantification. Separation procedures contemplated by the present invention include capillary electrophoresis, capillary zone electrophoresis, micellar electrokinetic capillary chromatography and/or various other forms of chromatography.

BACKGROUND OF THE INVENTION

Numerous clinical and research situations necessitate highly sensitive analytical methods for the analysis of amino acids, peptides, amino sugars and other primary amine bearing compounds. During the last twenty years a number of separation procedures have been developed allowing resolution of the components of a complex mixture of primary amines. Furthermore, methods of utilizing laser-induced fluorescence detection have been developed and refined, permitting detection of exceedingly small amounts of a fluorescent product. A continuing problem in the area of primary amine detection has been the design of reagents that not only react well with a variety of primary amines, but also yield a product which is readily detected in low amounts and is easily separable from a complex mixture of reactants and products.

A number of derivatizing reagents have been developed which add a chromophore, detectable at a specific wavelength of light, or a fluorophore which may be excited by light at a specific wavelength to emit light at a different wavelength. Some of these reagents include ninhydrin, fluorescamine, 7-chloro-4-nitro-benzene-2-oxa-1,3-diazole (NBD-chloride) and ortho-phthalaldehyde (OPA) (Rubenstein et al., 1979, Anal. Biochem. 95:117–121; Stein et al., 1974, Arch. Biochem. Biophys. 163:400–403; De Bernado et al., 1974, Arch. Biochem. Biophys. 163:390–399; Ghosh et al., 1968, Biochem. J. 108:155–160; Roth, 1971, Anal. Chem. 43:880–882; Lindroth et al., 1979, Anal. Chem. 51:1667–1674; Hodgin, 1979, J. Liq. Chromatogr. 2:1047–1059; and Deyl et al., 1986, J. Chromatogr. 379:177–250). OPA has been a popular reagent due to its ability to rapidly form intensely fluorescent isoindole products from non-fluorescent starting materials. However, the sensitivity of OPA analysis has been limited to the picomole range, and OPA derivatives are unstable due to their sensitivity to light, air oxidation and attack by acids (White et al., 1969, Adv. Heterocycl. Chem. 10:113–147). A newly developed reagent, naphthalene-2,3-dicarboxaldehyde (NDA) is structurally similar to OPA in that it has an ortho-dialdehyde moiety and it forms a fluorogenic isoindole product with a primary amine (De Montigny, 1987, Anal. Chem. 59:1096–1101). NDA forms a more stable isoindole product than OPA. The improved stability is partly due to the use of cyanide instead of thiol as a nucleophilic reagent, resulting in a nitrile group instead of a thiol group on the isoindole ring.

The above reagents usually allow detection in the picogram range when used with conventional separation systems such as liquid chromatography or high pressure liquid chromatography (HPLC) and non-laser fluorescence detection schemes. Sensitivity on this scale is inadequate for many current applications including, for example, the analysis of protein hydrolysates resulting from state-of-the-art protein microisolations. Improved separation techniques, such as capillary electrophoresis or capillary zone electrophoresis, especially when coupled with laser fluorescence detection, can increase the sensitivity of detection. However, in order to be useful for laser fluorescence detection, reagents must be developed which yield a product with an amine that is excitable by readily available lasers, for example the helium/cadmium laser or the argon ion laser.

To form isoindole products that are easily excitable at the output wavelengths of readily available lasers, a number of reagents have been synthesized, including unsubstituted 3-benzoyl-2-quinoline-carboxaldehyde (Beale, et al., 1989, Talanta 36:321–325) and 3-(2-furoyl) quinoline-2-carboxaldehyde (Beale, et al., 1990, J. Chromatogr. 499:579–587). While such reagents are fairly versatile when used in conjunction with liquid chromatography separation techniques, their utility with preferred separation techniques such as capillary electrophoresis is limited. This is apparently due to the relatively hydrophobic nature of the resulting isoindole products. Another significant problem with these reagents is that they also fail to react with most peptides consisting of more than three amino acids and with many amino sugars.

Hence, there is an outstanding need for reagents which 1) have the capability of reacting with large peptides, proteins and amino sugars, 2) yield products that are separable by modern micro-separation procedures, such as capillary electrophoresis, and 3) are detectable by commonly used laser detection systems. The XArQCA reagents of the present invention meet these three criteria.

SUMMARY OF THE INVENTION

The present invention is directed to a new class of 3-aroyl-2-quinoline-carboxaldehyde reagents, designated herein XArQCA reagents, for use in high sensitivity detection and quantification of naturally occurring or chemically synthesized primary amines such as amino acids, peptides, proteins, glycoproteins, amino sugars and pharmaceuticals.

Another aspect of the present invention provides for the chemical synthesis of the present XArQCA reagents.

Yet another aspect of the present invention provides for the incorporation of a primary amine into non-amine bearing compounds, such as carbohydrates, thereby allowing detection of these compounds by the present invention.

A further aspect of this invention is directed towards the isoindole products formed by reaction of the present reagents with primary amines.

A still further aspect of this invention is directed to separation of the isoindole products formed by reaction with the present reagents and a mixture of primary amines by micro-separation techniques, including capillary micellar electrokinetic capillary or capillary zone electrophoresis.

Another aspect of the present invention provides for the detection of the isoindole product formed by reaction with the present reagents and a primary amine by laser-induced fluorescence detection.

Yet another aspect of the present invention is directed towards the identification of a primary amine by comparison of its chromatographic or electrophoretic mobility after reaction with an XArQCA reagent, with that of known standards.

□ Gly—Gly—Try—Arg; ◊ Des—Asp$^1$-angiotensin I

Figure 4:
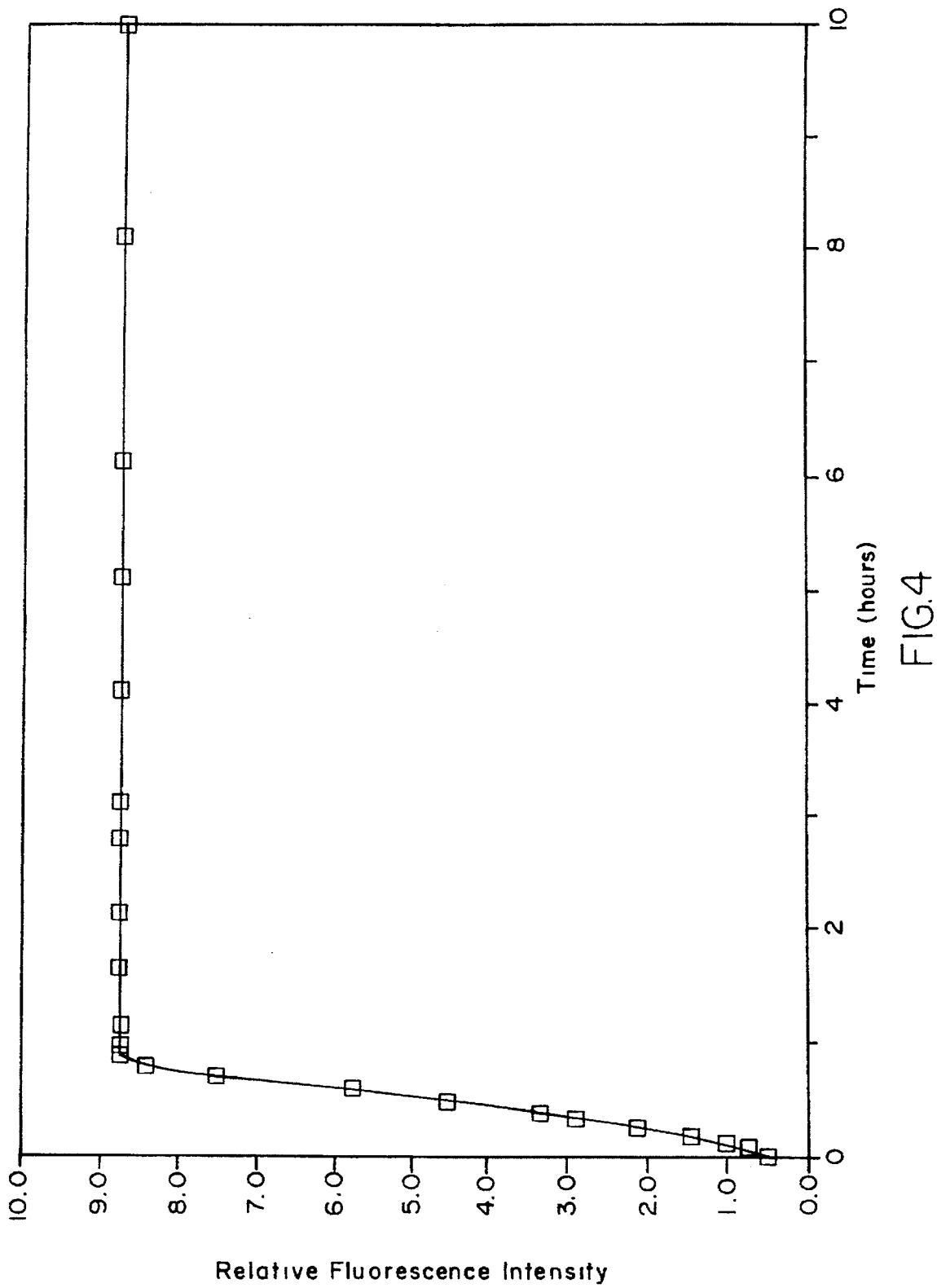

FIG. 4 depicts the stability of CBQCA-derivatized D(+)-galactosamine.

Figure 5A:
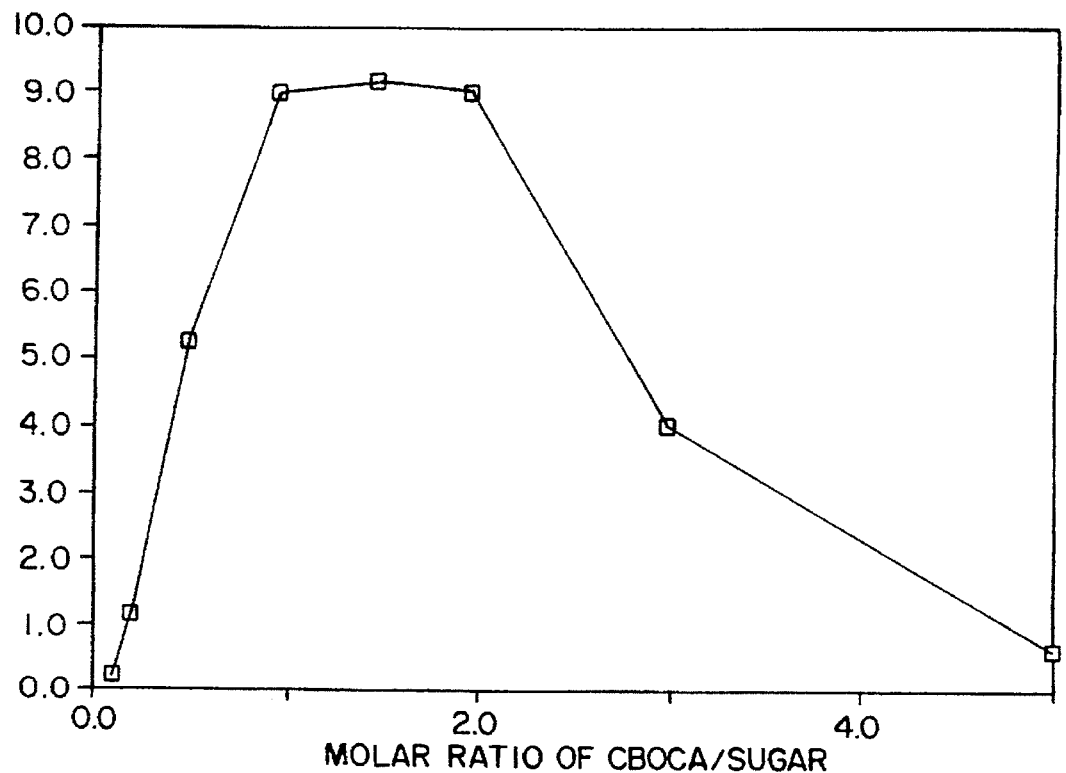
Figure 5B:
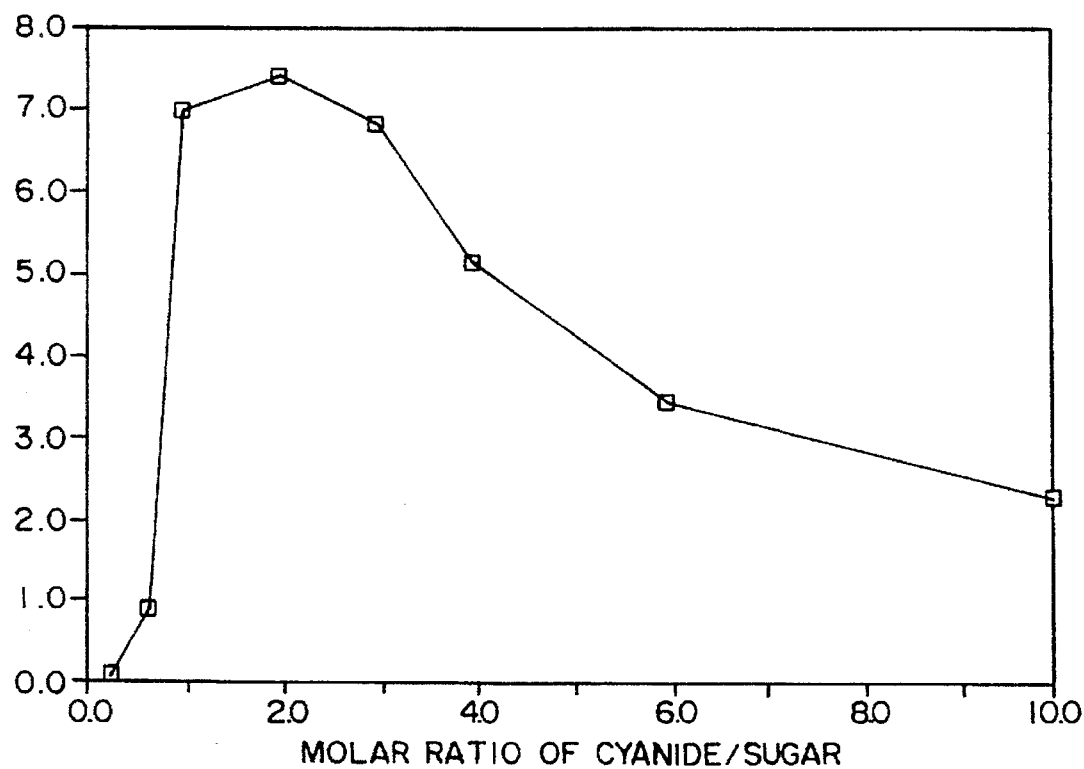

FIG. 5 depicts the effects of excess CBQCA reagent (A) and cyanide ion (B) on the relative fluorescence intensity of the product (CBQCA-D(+)-galactosamine).

Figure 6:
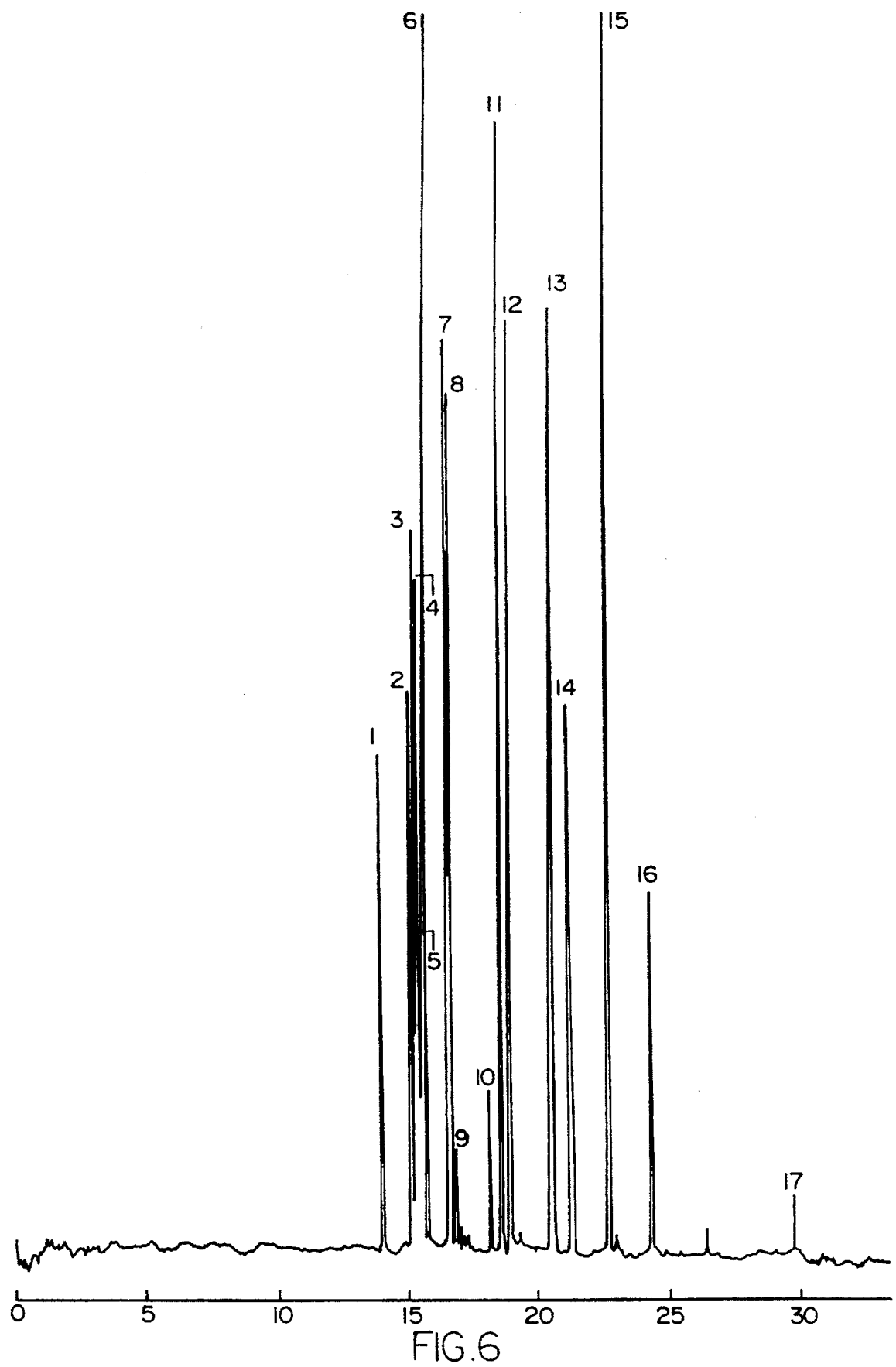

FIG. 6 depicts an electropherogram of standard amino acids derivatized by. CBQCA. Peak identification: 1: Arg; 2: Trp; 3: Tyr; 4: His; 5: Met; 6: Ile; 7: Gln; 8: Asn; 9: Thr; 10: Phe; 11: Leu; 12: Val; 13: Ser; 14: Ala; 15: Gly; 16: Glu; 17: Asp. Injection concentration for each amino acid is 8.71× $10^{-6}$M. Capillary: 50 μm i.d. (184 μm o.d.), 100 cm in length (70 cm to detector). Mobile phase: 0.05M TES buffer (pH-7.02), 50 μmM SDS. Operating voltage: 25 KV (14 μA).

Figure 7:
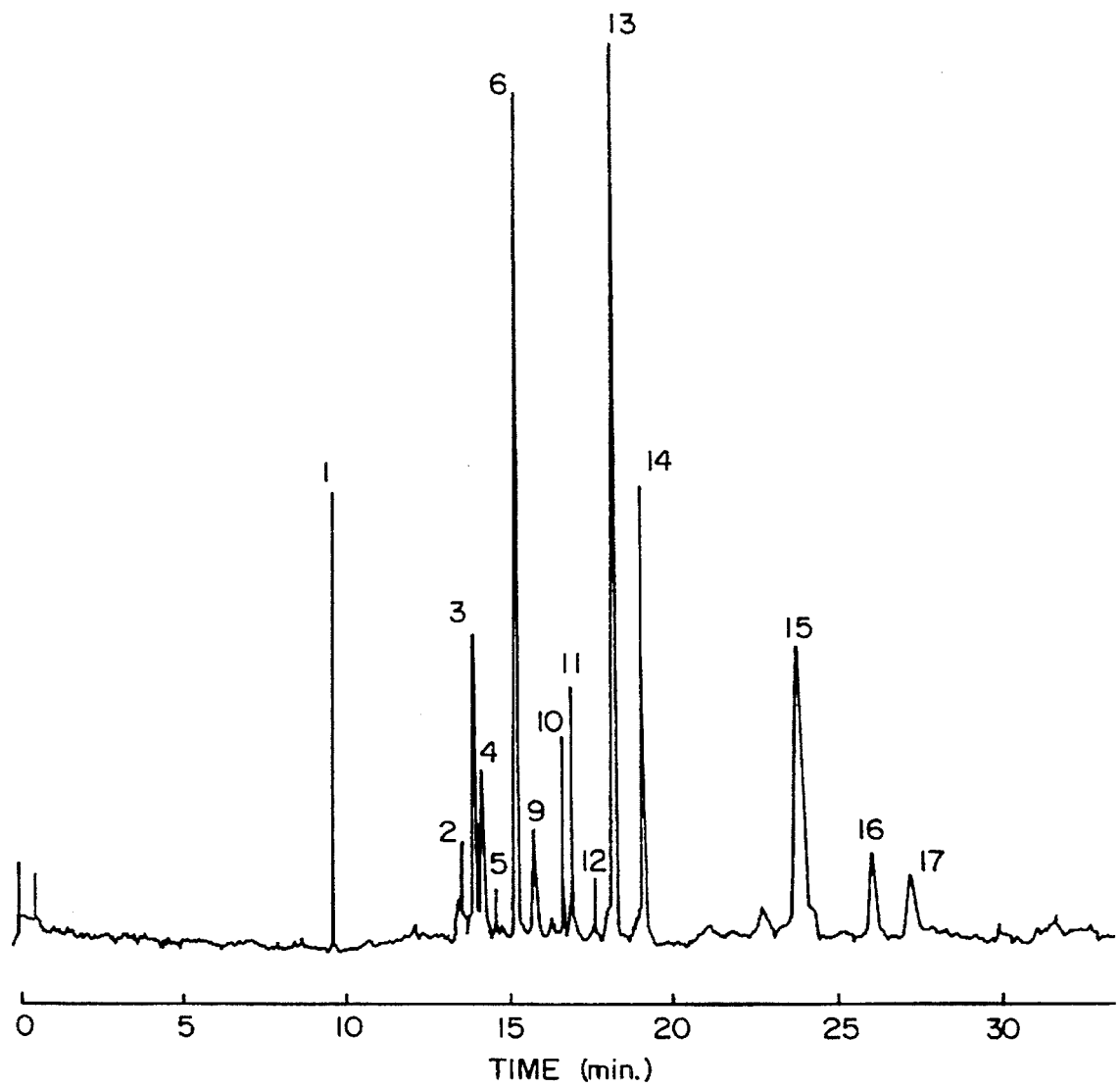

FIG. 7 depicts an electropherogram of amino acids from 1.9 pg (134 femtomole) of hydrolyzed lysozyme. Peak numbering and experimental conditions same as in FIG. 6.

Figure 8:
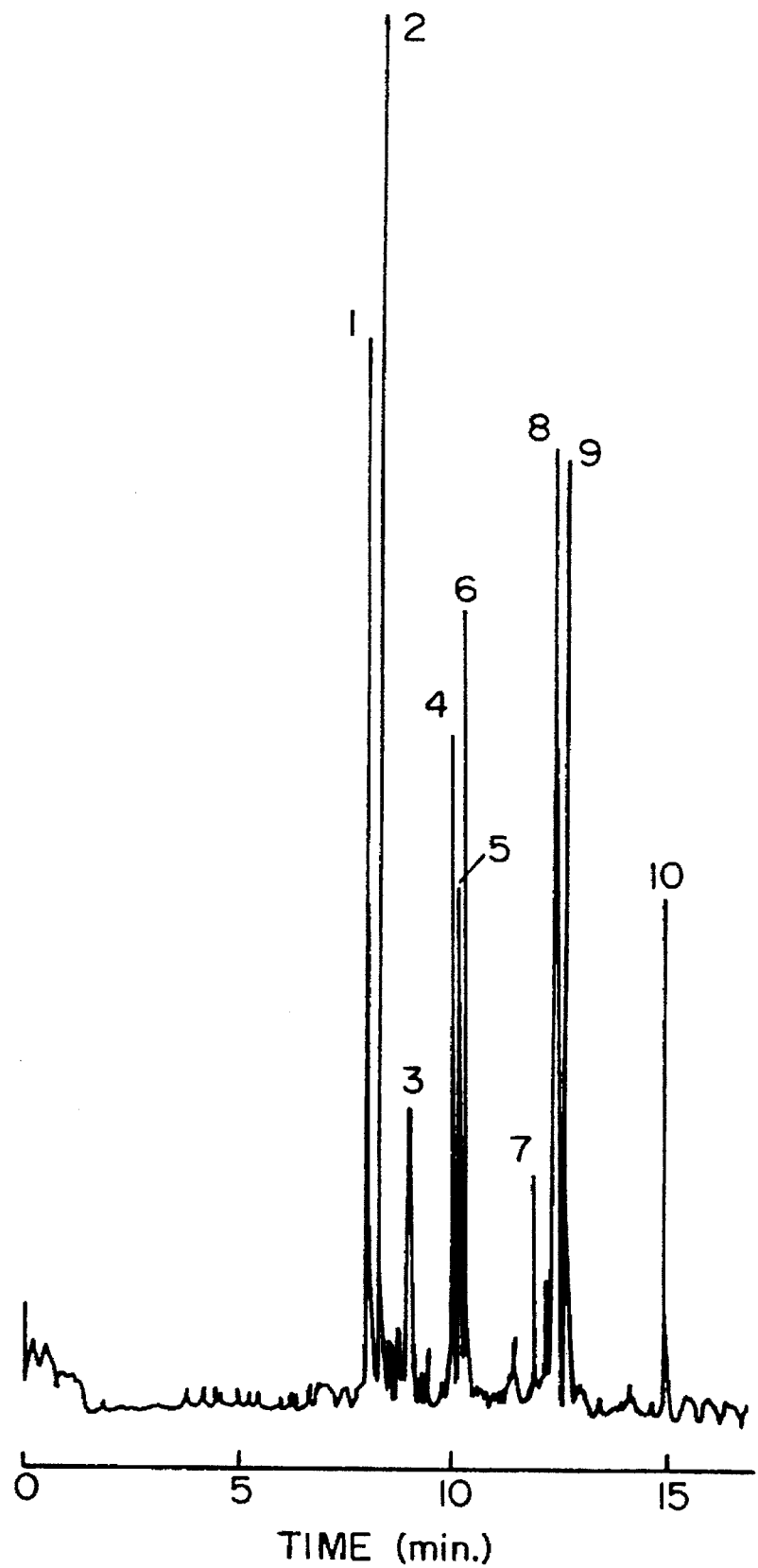

FIG. 8 depicts an electropherogram of standard peptides as CBQCA derivatives. Capillary: 50 μm i.d. (184 μm o.d.), 90 cm in length (60 cm to detector). Mobile phase: 0.05M borate buffer (pH-9.50), 20 mM α-cyclodextrin. Peak identification: 1: Ile$^7$-Angiotensin III; 2:Gly-Gly-Tyr-Arg; 3: Val$^5$-Angiotensin II; 4: Gly-Leu-Tyr; 5: Met-Leu-Tyr; 6: Val-Ala-Ala-Phe; 7: Val-Gly-Ser-Glu; 8: Glu-Gly-Phe; 9: Glu-Val-Phe; 10: Val-Gly-Asp-Glu. Operating voltage: 20 KV (7 μA).

Figure 9:
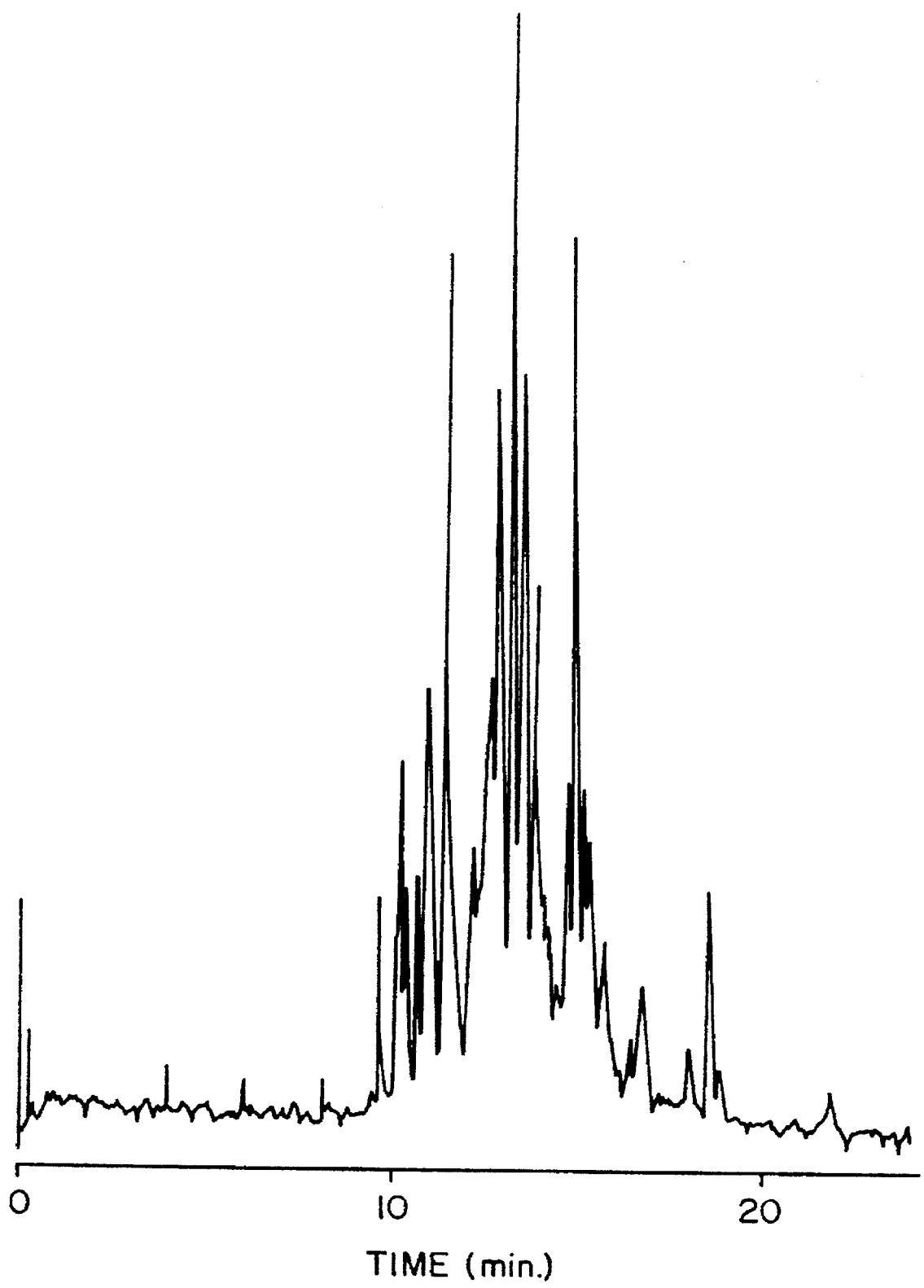

FIG. 9 depicts an electropherogram of peptides from 17 femtomoles (392 pg) of tryptic-digested B-casein.

FIG. 10 depicts the effect of borate on the electrophoretic separation of structurally related amine sugars 1=D (+)-glucosamine; 2=D (+) galactosamine.

A) buffer: 0.04M Na$_2$HPO$_4$/Tris-HCl, pH 9.10 applied voltage: 20 kV (8 μA)

B) buffer: 0.02M Na$_2$B$_4$O$_7$–10 H$_2$O/0.02M Na$_2$ HPO$_4$, pH 9.12 applied voltage: 24 kV (9 μA)

Figure 11:
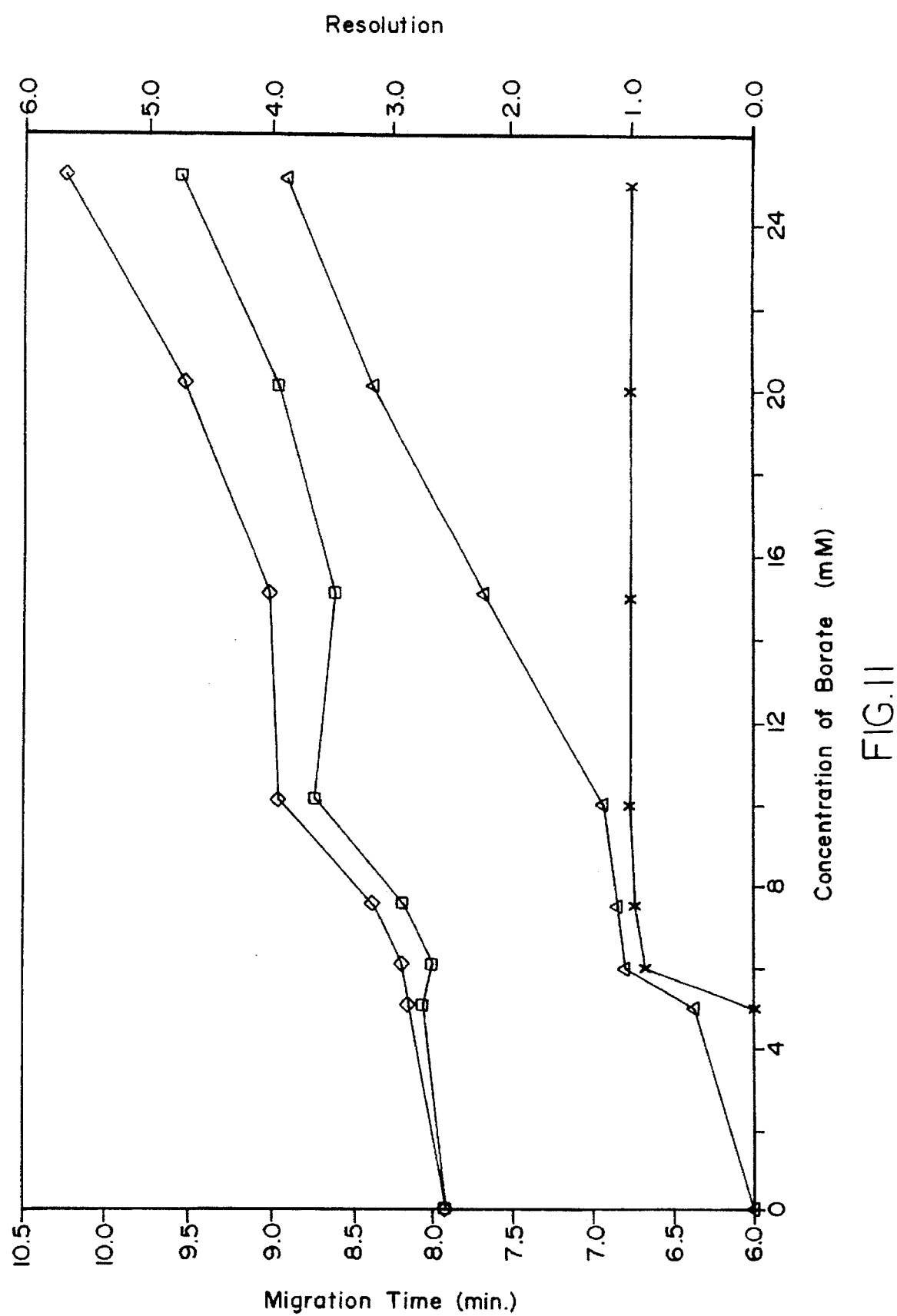

C) Same as (B) except the sample solution was kept for more than three days at room temperature FIG. 11 depicts the effects of borate concentration on migration time and peak resolution of two structurally related amino sugars.

□=D (+)-glucosamine

◊=D (+)-galactosamine

Δ,X=measured parameters related to peak resolution

Figure 12:
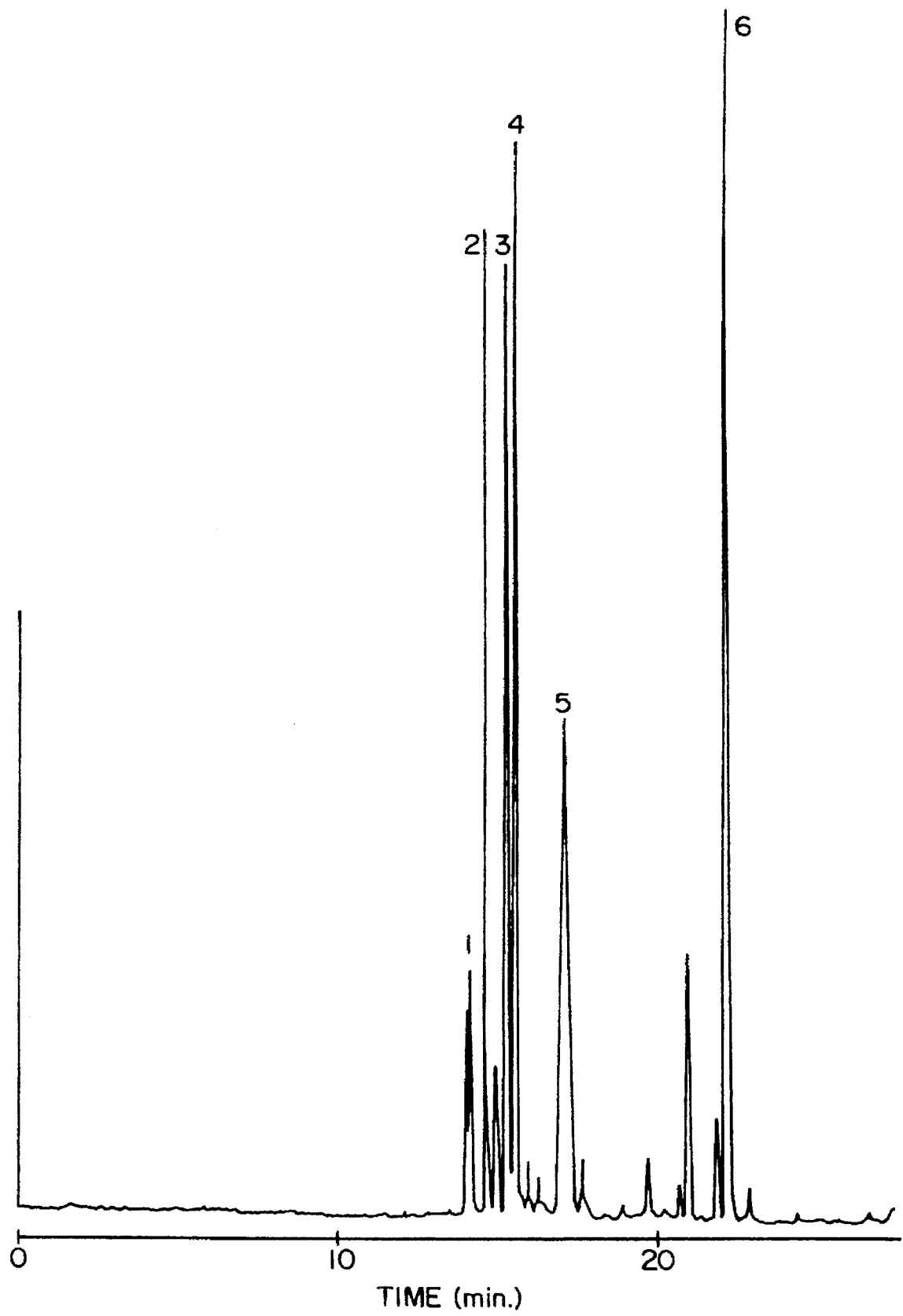

FIG. 12 depicts an electrophoretic separation of six model amino sugars derivatized by CBQCA. (Buffer: 20 mM Na$_2$HPO$_4$/20 mM borate/50 mM SDS, pH=9.12.)

1: 1-amino-1-deoxy-glucose;

2: 1-amino-1-deoxy-galactose;

3: 2-amino-2-deoxy-glucose;

4: 2-amino-2-deoxy-galactose;

5: 6-amino-6-deoxy-glucose;

6: D-galactosaminic acid.

FIG. 13 depicts an electrophoretic pattern of an amino polysaccharide (N-deacylated chitin with molecular weight 750,000) which has been hydrolyzed under two different conditions.

A=hydrolysis in concentrated HCl at 100° C. for 34 hours.

B=hydrolysis in 0.2N HCl heated at 100° C., followed by addition of an equal volume of concentrated HCl and heating at 100° C. for 34 hours.

FIG. 14 depicts the effect of reaction temperature, of NaBH$_3$CN concentration, reaction time and the effect of ammonium ion concentration on the effectiveness of amine addition to monosaccharides. The relative amount of amine addition was detected by subsequent derivatization with CBQCA.

FIG. 15 depicts electrophoretic separation of monosaccharides mixtures derivatized by CBCQA after amination.

A) Peak assignment: 1-CBQCA-mannose, 2-CBQCA-glucose, 3-CBQCA-galactose

B) Peak assignment: 1: D (+)-glucosamine; 2: D (+)-galactosamine; 3: D-erythrose; 4: D-ribose; 5: D-talose; 6: D-mannose; 7: D-glucose; 8: D-galactose; 9: impurity; 10: D-galacturonic acid; 11: D-glucuronic acid; 12: D-glucosaminic acid; 13: D-glucose-6-phosphate.

FIG. 16 depicts an analysis of monosaccharides released from bovine fetuin by acidic hydrolysis. (A) Peak assignment: 1-CBQCA-glucosamine; 2-CBQCA-galactosamine; 3-unknown. Amino sugars were released with 4M hydrochloric acid at 100° C. for 6 h, and subsequently derivatized by CBQCA. Peak assignment for (B)–(D): 1: N-acetylglucosamine; 2: N-acetylgalactosamine; 3: mannose; 4: fucose; 5: galactose; 6: galacturonic acid (internal standard). (B) standard mixture of monosaccharides, (C) hydrolysate by 2.0M trifluoroacetic acid, (D) hydrolysate by 4.0M HCl.

Figure 17:
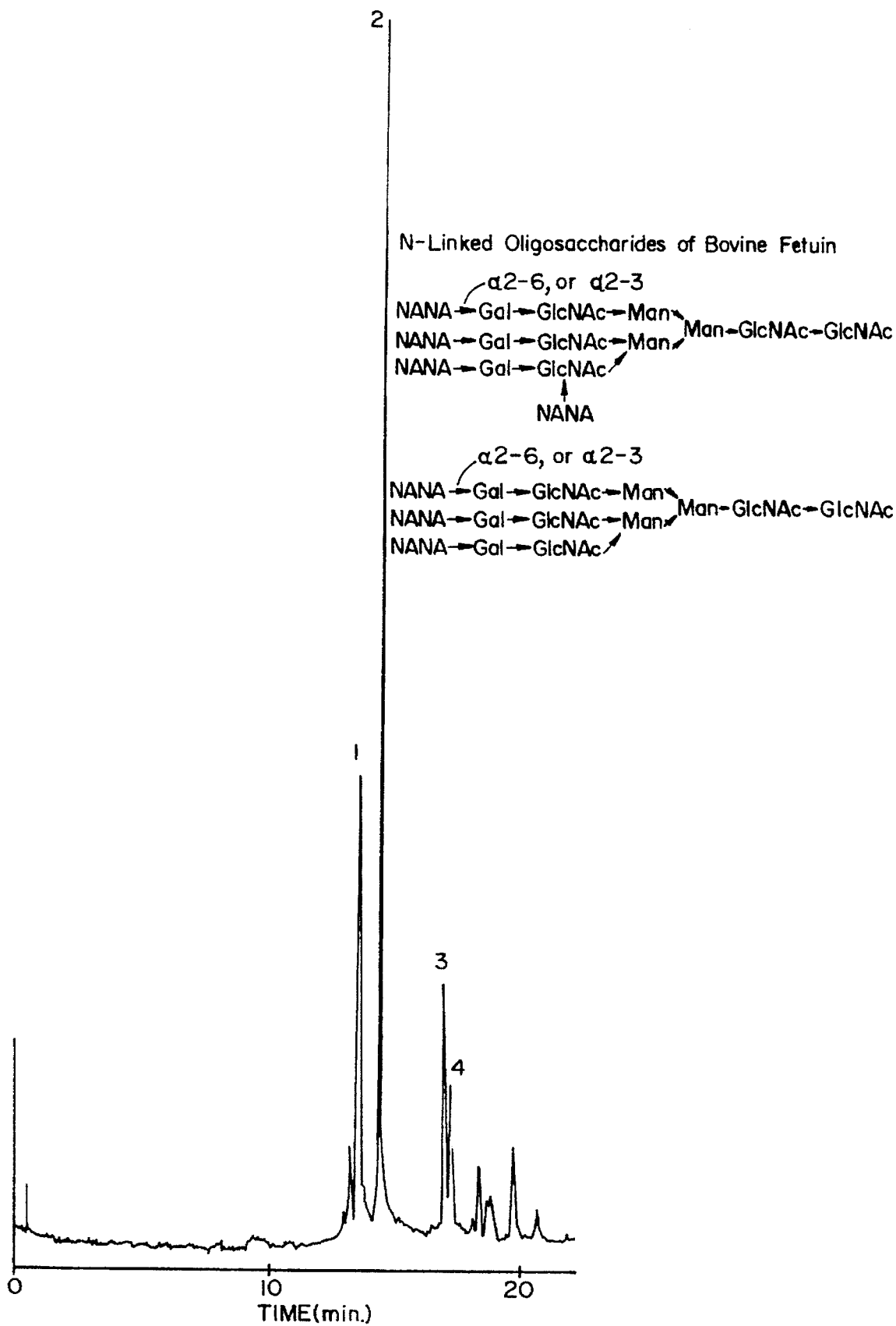

FIG. 17 depicts an analysis of N-linked oligosaccharides released from bovine fetuin by anhydrous hydrazine. Substituents: NANA: N-acetylneuraminic acid; Gal: galactose; GlcNAc: N-acetylglucosamine; Man: mannose.

DETAILED DESCRIPTION OF THE INVENTION

The present invention provides a highly sensitive method of detecting primary amines by reaction of the amines with novel substituted aroyl-2-quinoline-carboxaldehyde (XArQCA) reagents, followed by separation and measurement of the reaction products. The XArQCA reagents of the present invention have the general formula:

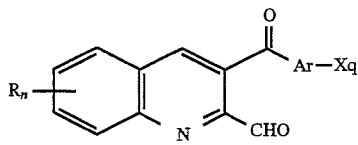

or a salt thereof, wherein

Ar is an aryl or heteroaromatic group, one of R or X is an ionizable group and the other is hydrogen, lower alkyl, aryl or aryl-lower alkyl, alkoxy, diloweralkylamine or piperidinyl, n and q are independently 0–5, provided that at least one ionizable group is present.

The term aryl refers to an aromatic moiety containing 6–10 ring carbon atoms and includes phenyl, α-naphthyl, β-naphthyl, and the like.

The heteroaromatic rings as used herein, wherein singularly or in combination with other groups include cyclic rings which may be saturated, partly unsaturated or heteroaryl, and contain one or two hetero ring atoms. The heterocyclic rings include the benzo heterocyclics. The heterocyclic ring contains from 5–14 ring atoms. It is further preferred that the heterocyclic group contains 1, 2 or 3 heteroatoms selected from N, S or O and contains at least carbon ring atoms. It is preferred that the heterocyclic ring is monocyclic and contains 5 or 6 ring atoms. Typical examples include thienyl, furyl, tetrahydrofuryl, oxazolyl, benzoxazolyl, pyrrolyl, pyridyl, imidazoyl, benzothienyl, pyranyl, pyrazolyl, pyrazinyl, indolyl, pyrimidinyl, isoquinolyl, quinolyl, piperidyl, pyridazinyl, indolinyl, morpholinyl and the like. The preferred heteroatoms are N, 0 or S. In a preferred form the heterocyclic ring is an oxygen containing heterocyclic ring.

There are up to 7 positions available on the present aryl groups for substitution by the X groups of the present invention.

Phenyl and furyl groups are preferred Ar groups.

As used herein, the term ionizable group refers to an organic moiety that is inherently charged or is capable of losing a proton at pH 6 to 10 in aqueous solution. Such groups include organic acids such as alkyl carboxylic acids, alkyl sulfonic acids, alkyl sulfinic acids, and alkyl phosphonic acids, as well as other groups like phenols, thiols, quaternary amines, amidinium salts, imides, beta-diketones, nitroalkanes and the like. Preferred include $(CH_2)_m COOH$, $(CH_2)_m OH$, $(CH_2)_m SO_3H$, $(CH_2)_m SO_2H$ $(CH_2)_m SH$, $CH_3-(CH_2)_{m1} SO_3H$,

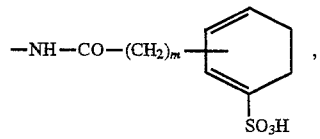

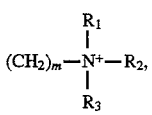

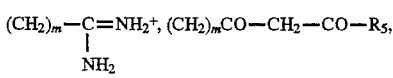

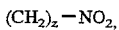

and the like, wherein m and $m_1$ are independently 0–5 and z is 1–5. $R_1$, $R_2$, $R_3$, and $R_5$ are independently lower alkyls.

Said term also includes the salts of said ionizable groups. These compounds form basic salts with various organic and inorganic bases. Among the salts which may be prepared are ammonium salts, alkali metal salts, alkaline earth metal salts and the like.

For groups such as the nitroalkanes, nitrodiketones and the imides, the hydrogen on the α-carbon to nitroalkane and the hydrogen which is on the α-carbon to the C=O can be removed by base and are thus the ionizable hydrogens.

The term lower alkyl refers to alkyl groups containing one to six carbon atoms. These groups may be straight-chained or branched, and include such moieties as methyl, ethyl, propyl, isopropyl, n-butyl, such-butyl, iso-butyl, t-butyl, pentyl, amyl, hexyl and the like. The preferred alkyl groups are $C_1$–$C_4$ alkyl. The most preferred alkyl group is methyl.

An aryl-lower alkyl refers to an aryl group with one or more lower alkyl substituents.

The term alkoxy refers to a lower alkyl covalently bonded to an oxygen atom which in turn is bound to the aryl or heteroaromatic (Ar) moieties of the present XArQCA reagents. Methoxy is the preferred alkoxy.

A dialkylamine group as used herein is an amine with two lower alkyl groups wherein the amino nitrogen is bound to the aryl or heteroaromatic (Ar) residues of the present XArQCA reagents.

The subscripts, n and q define the number of R and X groups, respectively. The R substituents may be present on the 5, 6, 7, 8, or 9 positions of the quinoline ring; X substituents may be present on any of the unoccupied positions of the aryl or heteroaromatic (At) rings. For example, n may be 0–5 since the quinoline moiety has 5 ring positions open for substitution. Hydrogen is found in place of an R or X group if n is less than 5, or if q is less than the number of positions available for substitution. If there is more than one R or X group on an XArQCA reagent then each R or X group may be the same or may be different. When R or X is not an ionizable group, it is preferably methyl or hydrogen; hydrogen is most preferred.

As used herein, m, and ml, are integers. The value of these integers determines the number of times the group is repeated. For example, when ml is 2, there are two $CH_2$ groups. It is preferred that m is 0. The most preferred value of $m_1$ is 1, 2, and especially 3.

Preferred XArQCA reagents are depicted below:

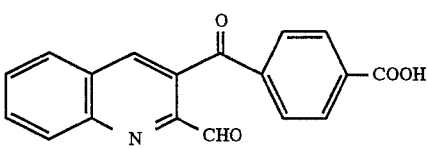

A)

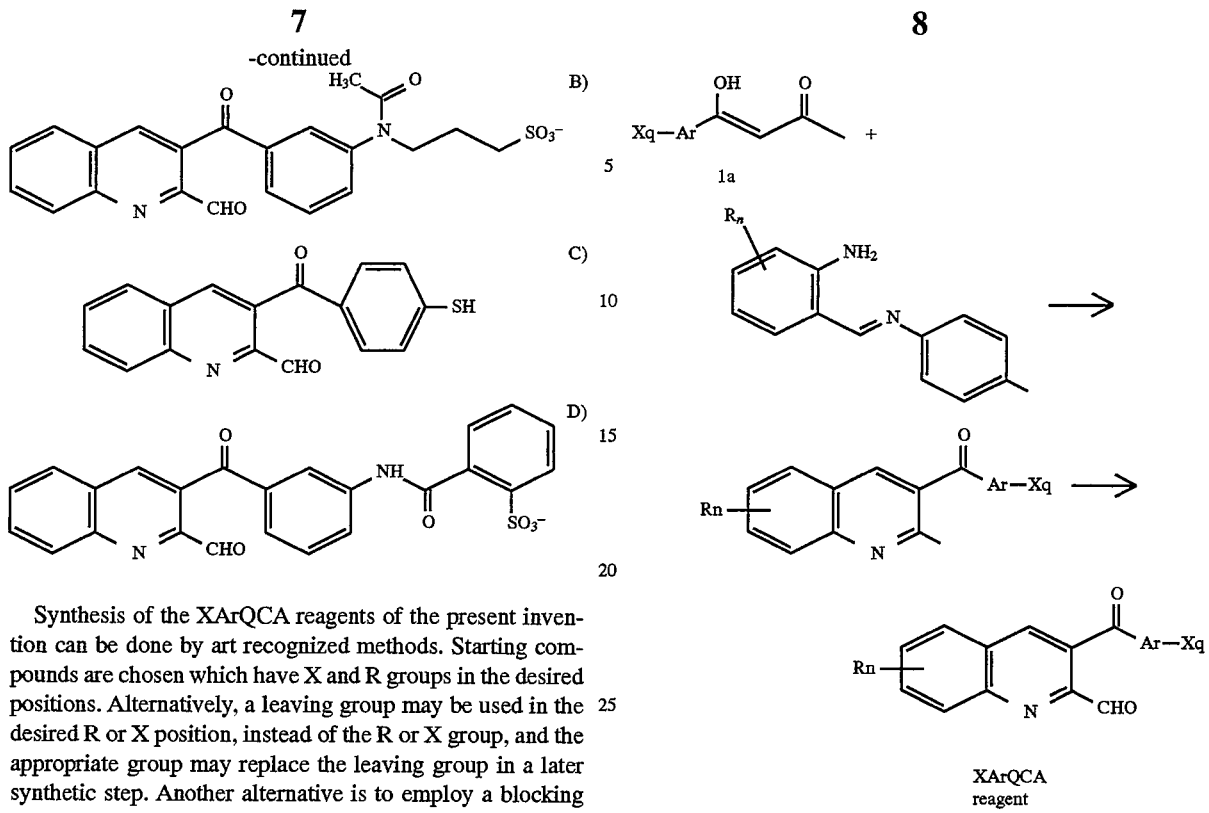

Synthesis of the XArQCA reagents of the present invention can be done by art recognized methods. Starting compounds are chosen which have X and R groups in the desired positions. Alternatively, a leaving group may be used in the desired R or X position, instead of the R or X group, and the appropriate group may replace the leaving group in a later synthetic step. Another alternative is to employ a blocking group on a reactive group which may be present within the X or R substituent. The use of leaving or blocking groups prevents undesirable side reactions from occurring while permitting desired reactions to take place.

As is generally known in the art, and for the purposes of the present invention, a leaving group is defined as a group which is readily broken away from its union with a carbon atom. These groups are readily recognizable by one skilled in the art. Suitable leaving groups are generally electron attracting groups, either because of their electronegativity or because they have an inductive effect, and may include groups such as halides, $N_3$, HO-Aryl, or $HSO_3$-Aryl groups, and the like.

A blocking group is covalently bound to a reactive group to render the reactive group unreactive while allowing desired reactions to take place. To be useful, a blocking group must be easily removed without chemically altering the remainder of the molecule, thereby regenerating the correct structure of the reactive group. Examples of blocking groups effective with, for example, primary and secondary amino groups include carbobenzoxy (cleaved by catalytic hydrogenation), tert-butoxycarbonyl (cleaved by mild acid treatment) and 9-fluorenylmethoxycarbonyl (cleaved by secondary amines). Aryl alcohols may be protected with, for example, benzoyl or acetyl blocking groups. The synthetic steps for many of the present XArBQCA reagents will not affect many of the present X or R groups, therefore blocking groups may not be required.

Compounds of the present invention can be prepared by art recognized techniques. For example, the keto-enol compound of Formula 1a can be coupled with a substituted 2-amino-N-(p-tolyl)benzaldimine and the resulting product is oxidized by an oxidizing agent, such as $SeO_2$, or the like, as depicted hereinbelow.

Compound 1a is the enol form of the dicarbonyl depicted below (1b):

The dicarbonyl (1b) may be formed by condensing an alkyl benzoate, e.g., methyl benzoate, with acetone in the presence of a strong base, such as sodium amide or sodium hydride and the like, as is depicted for the formation of 3, below.

The reagent, 2-amino-N-(p-tolyl)benzaldimine can be made by condensing p-toluidine with o-nitrobenzaldehyde followed by reduction of the nitro group as depicted below.

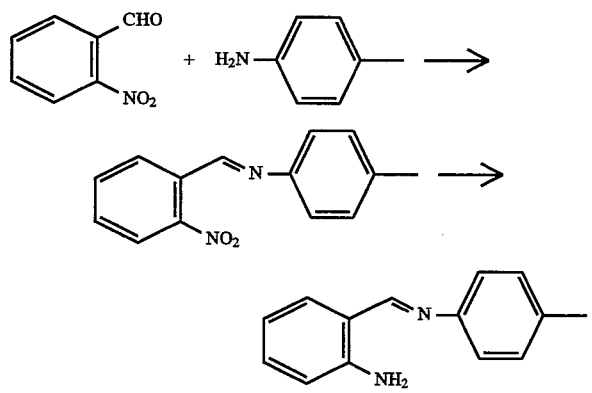

Further exemplary, procedures for forming the compounds of the present invention are depicted hereinbelow. For example, 3-(4-carboxybenzoyl)-2-quinoline carboxaldehyde and 3-(4-sulfhydrylbenzoyl)-2-quinolinecarboxaldehyde may be prepared by starting with methyl 4-cyanobenzoate as follows.

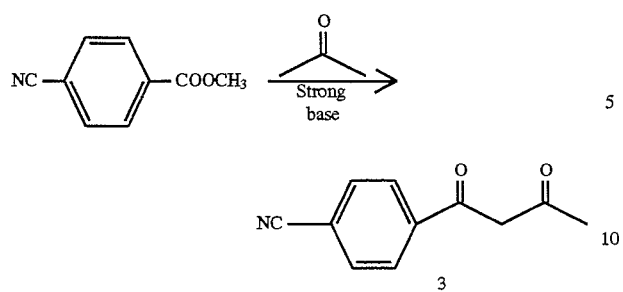

To create the quinoline moiety, 3 may be reacted with 2-amino-N-(p-tolyl)benzaldimine, thereby generating 3-(4-cyanobenzoyl)-2-methylquinoline (4a).

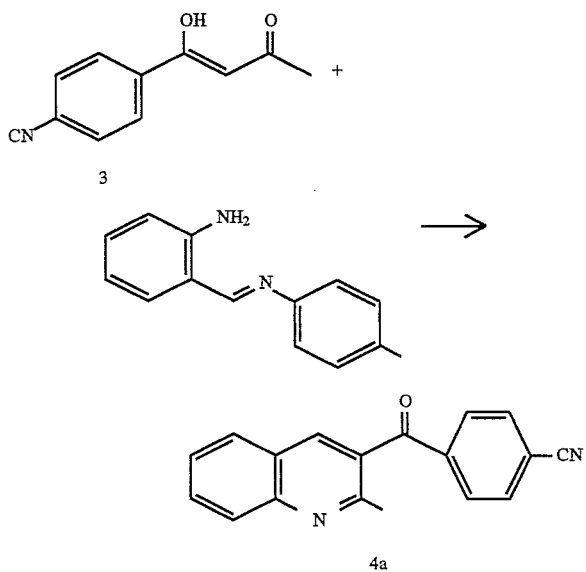

The cyano group may be made into a carboxylate group by strong alkaline treatment, to create 3-(4-carboxybenzoyl)-2-methylquinoline (5a).

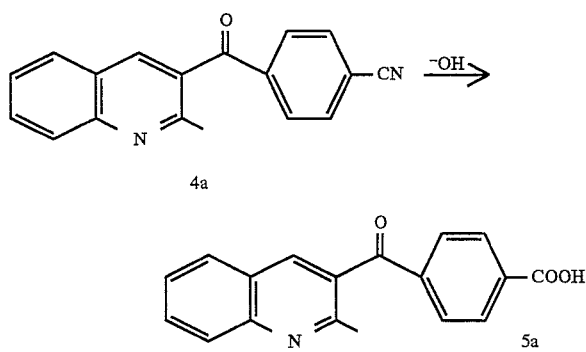

Alternatively, an iodo group present on the intermediate depicted below (4b) may be replaced by a sulfhydryl group treatment of 4b with $(NH_2)_2CS$, to generate 3-(4-sulfhydrylbenzoyl)-2-methylquinoline (5b)

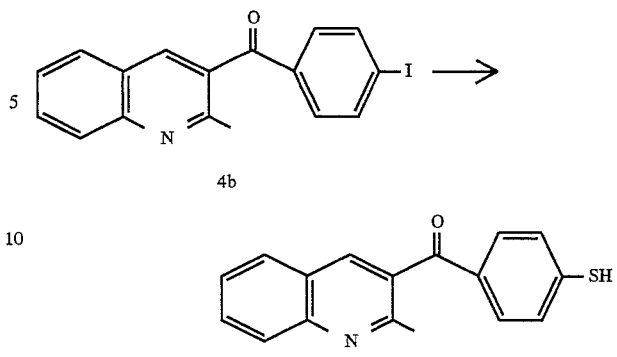

The intermediate 4b can be prepared by reacting 2-amino-N-(p-tolyl)benzaldimine with the p-iodobenzyl dicarbonyl depicted below. This dicarbonyl is made by a reaction similar to that depicted on page 15, but using methyl 4-iodobenzoate in a reaction with acetone in strong base.

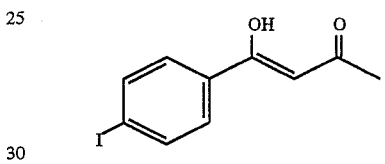

Finally, the methyl groups on the quinoline moieties of 5a and 5b may be oxidized to an aldehydes by treatment with selenium dioxide to generate 3(4-carboxybenzoyl)-2-quinolinecarboxaldehyde or 3(4-sulfhydrylbenxoyl)-2-quinolinecarboxaldehyde (preferred reagents A and C, respectively).

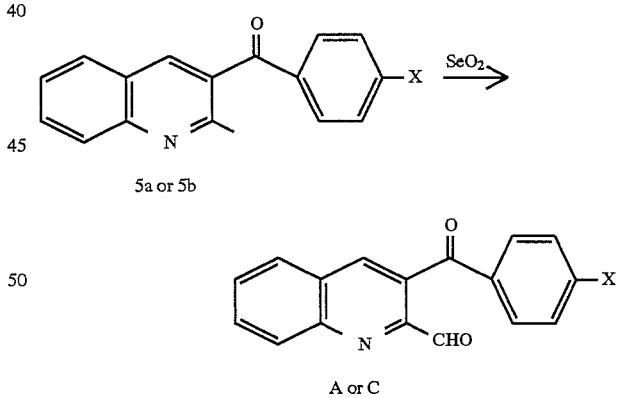

Synthesis of preferred XArQCA reagents wherein X is in the meta position may be effected by methods similar to those described above. For example, (3-nitrobenzoyl) acetone (6) can be prepared by nitration of benzoyl acetone by D standard techniques known to one skilled in the art. (3-nitrobenzoyl)acetone 6 can then be reacted with 2-amino-N-(p-tolyl)benzaldimine, to generate 3-(3-nitrobenzoyl)-2-methylquinoline (7). The nitro group on may be reduced by reaction with a reducing agent under acidic conditions. The product is 3-(3-aminobenzoyl)-2-methylquinoline (8).

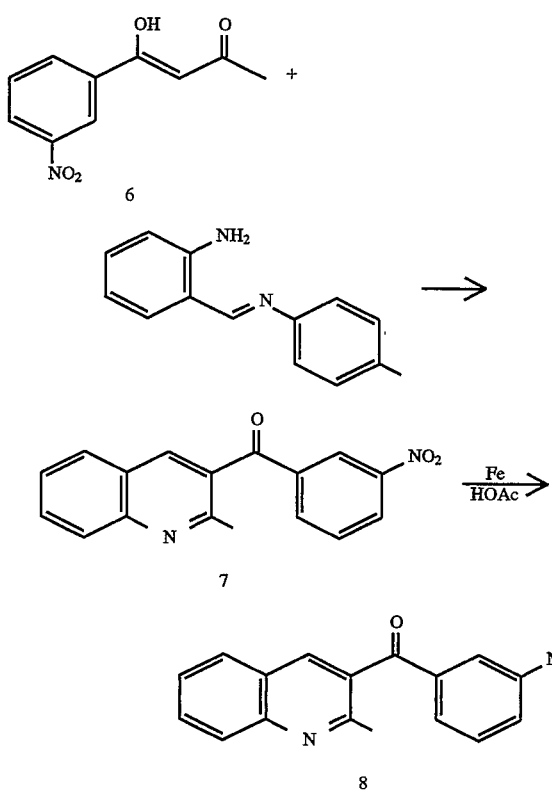

To generate preferred reagent B, 3-(3-aminobenzoyl)-2-methylquinoline (8) may be reacted with γ-propanesultone and acetic anhydride to generate 9. The methyl group on the quinoline moiety of 8 may then be oxidized by treatment with selenium dioxide, thereby generating preferred reagent B.

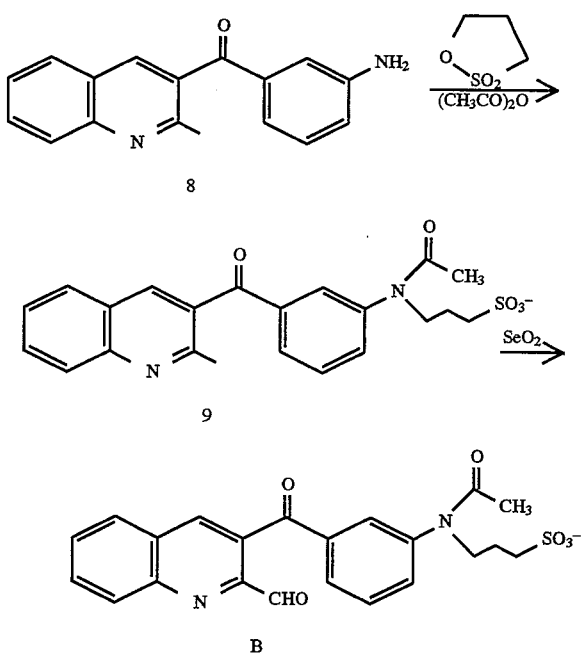

Similarly, to generate preferred reagent D, 3-(3-aminobenzoyl) 2-methylquinoline (8) may be reacted with the reagent, 2-sulfobenzoic anhydride depicted below, and then the quinoline methyl group oxidized as described above.

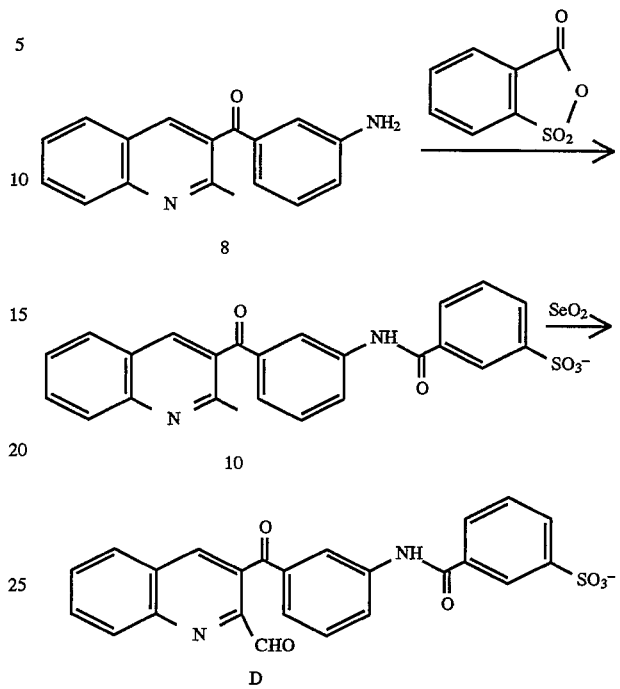

These reactions are generally performed in inert solvents, such as methylene chloride, chloroform and THF, dioxane and the like. It is preferred that the reaction be run in THF. They may be run at temperatures ranging from room temperature up to reflux temperatures.

Therefore, the class of compounds disclosed here are aroylaraldehydes which have a number of aromatic or heterocyclic rings, or various substituents on these rings that cause strong light absorption after reaction with primary amines, and which also possess ionic or ionizable functional groups to permit satisfactory migration in electrophoresis and micellar electrokinetic chromatography, or ionic interaction in various components of chromatography.

A method of determining the presence of a primary amine includes reacting the primary amine with an appropriate amount of an XArQCA reagent in the presence of an alkali cyanide and then detecting the product of the reaction. An example of such a reaction is depicted below.

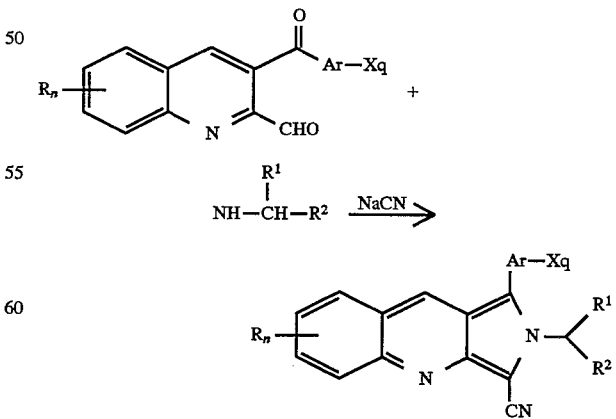

The $R^1$-CH-$R^2$ group represents any organic moiety; most commonly it may be any naturally occurring or chemically synthesized sugar or pharmaceutical; another common alternative is that $R^1$ may be $COOR^3$, wherein $R^3$ is hydrogen, an amino acid or peptide, and $R^2$ may be a side chain of a naturally occurring or chemically synthesized amino acid.

As used herein, the term amino acid includes the naturally occurring amino acid. Naturally occurring amino acids are alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine, 4-hydroxyproline, naphthylalanine, 5-hydroxylysine, -(-N-methyllysine, 3-methylhistidine, desmosine, isodesmosine, homocysteine, homoserine, citrulline, ornithine, canavanine, djenkolic acid, and β-cyanoalanine. Common amino acids which are chemically synthesized include penicillamine, amongst others.

As used herein the term primary amine includes alkyl amines (containing one to six carbon atoms), amino acids, peptides, proteins glycoproteins, amino sugars and pharmaceuticals, as well as molecules to which a primary amine may be easily incorporated, such as reducing sugars, and polysaccharides, many of these amines will be described or discussed in more detail below.

As an example of the detection limits of the present invention, glycine and galactosamine have been measured at $1 \times 10^{-18}$ and $5 \times 10^{-19}$ moles, respectively, using 3-(4-carboxybenzoyl)-2-quinolinecarboxaldehyde (preferred reagent A) and a helium/cadium laser detection system.

Peptides readily react with the present reagents in a general reaction depicted below.

molecular sizes, necessitating separation by electrophoretic or chromatographic methods. A "peptide map", is the resulting separation pattern characteristic of a given protein molecule. The reagents and procedures disclosed herein provide peptide maps from extremely small amounts of protein materials. For example, a tryptic peptide map of B-casein, in which the fragment peptides were labeled through the action of CBQCA, separated electrophoretically, and detected by the laser-induced fluorescence technique, allowed detection of just 17 femtomoles of digested protein.

Amino sugars, for example galactosamine, depicted below, may also be detected in small quantities.

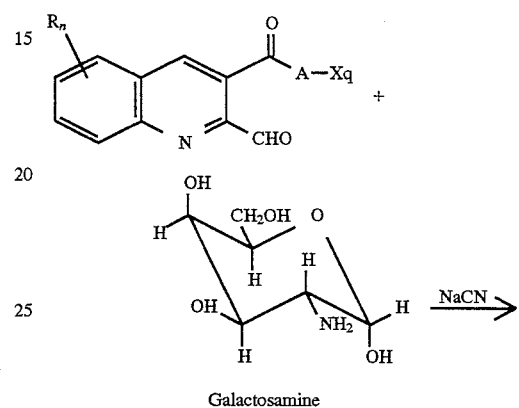

Galactosamine

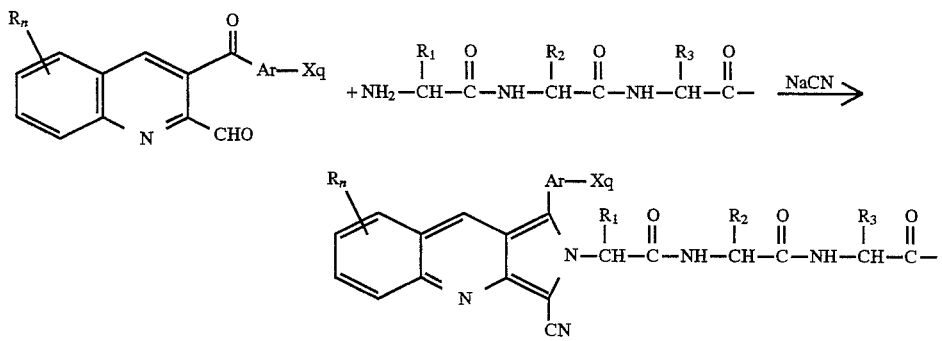

The $R_1$, $R_2$ and $R_3$ groups depicted on the peptide of this reaction are any of the side groups commonly found on naturally occurring or chemically synthesized amino acids. The term peptide as used herein, is a fragment of a protein including dipeptides, tripeptides and any portion of a protein that is somewhat less than the whole. The number of amino acids in a peptide may range from 2–50, and preferably 2–25. It is preferred that the peptide consists of naturally occurring amino acids.

Proteins may be structurally analyzed by peptide mapping through the use of the methods provided by the present invention. Peptide maps are generated from various protein molecules to characterize the protein structurally or prove the identity of a protein type. In a general procedure, a protein molecule is subjected to site specific cleavage, by a suitable agent, to yield a reproducible set of fragment peptides. For example, trypsin is among the most common site-specific reagents causing cleavages at the lysine and arginine sites of a protein molecule. Alternative treatment procedures cleave polypeptides at different amino acids. Site specific cleavage yields a mixture of peptides with varying -continued

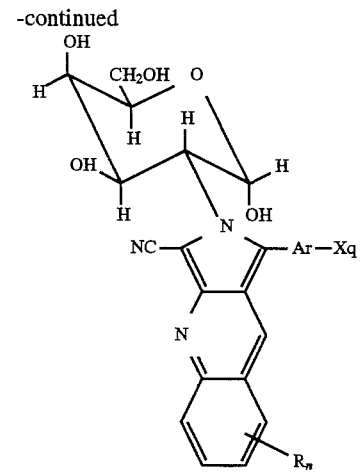

Derivatized galactosamine is detected at about $5 \times 10^{-19}$ mole when using the methods of the present invention.

Primary amines react readily with the XArQCA reagents of the present invention. Primary amines contemplated for detection by the present invention include amino acids, peptides, protein, amino sugars, pharmaceuticals and any other molecule with one or more primary amine. However, the present invention is not limited to detection of molecules which naturally possess a primary amine. A primary amine may be added to a molecule, to allow detection by the present invention. A number of procedures, known to one skilled in the art, may be used to add a primary amine to or create a primary amine within a molecule. For example, a cyano or nitro group may be reduced to an amine. Since cyano and nitro groups are easily added to unsaturated bonds, primary amines may frequently be added to unsaturated organic molecules via addition of a cyano or nitro group, followed by reduction to an amine.

Reductive amination of aldehydes is another, very useful, procedure for creating a primary amines in a variety of molecules, including carbohydrates. Bioanalytical methodologies in the carbohydrate field have lagged behind analytical developed for other biological macromolecules. Yet sugar moieties in glycoproteins and other biomolecules have wide ranging importance as they are involved in processes such as protein targeting, cell-cell recognition, cell migration, antigen-antibody interaction and the function of receptor proteins. Hence, there is a long standing need in the prior art for highly sensitive techniques capable of detecting the minute amounts of carbohydrates in glycoprotein samples.

A general reaction depicting the reductive amination of a carbonyl is shown below.

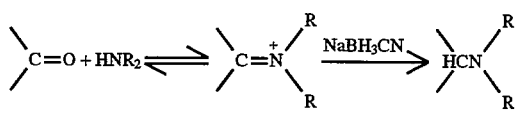

Since primary amines are desired for subsequent reaction with the present XArQCA reagents, ammonium ion is typically used as an amine source. Any ammonium salt may be used; $(NH_4)_2SO_4$ or $NH_4Cl$ are common examples. Reducing sugars are particularly amenable to reduction amination, yielding an amino sugar which is readily derivatized by the present XArQCA reagents.

In an analysis of the carbohydrate moieties of a glycoprotein one must distinguish amino sugars naturally present on the glycoprotein from non-amino sugars. The must common glycoproteins contain two neutral non-amino sugars, mannose and galactose, and two amino sugar derivatives, N-acetylglucosamine and N-acetylgalactosamine. The non-amino sugars can be easily released from a glycoprotein by hydrolysis with 2.0M trifluoroacetic acid in 6 hours at 100° C. For a complete release of amino sugars, stronger acidic conditions are needed. For example, a glycoprotein may be hydrolyzed by 4.0M HCl for 6 hours at 100° C., generating all types of sugars, including amino sugars which have lost their acetyl groups during hydrolysis. If the amino acids and peptides are removed from the mixture, amino sugars can be directly determined by the present fluorescent derivatization techniques and the non-amino sugars will not be detected. To analyze the non-amino sugars, hydrolysis by either method may be done and the amine groups of the released amino sugars can be blocked by acetylation. N-acetylation prevents derivatization of primary amines by the present XArQCA reagents. Reductive amination may then be used to provide amine groups to the non-amino sugars; these sugars may then be derivatized with an XArQCA reagent and detected by the methods of the present invention.

The present invention is not limited to simple detection and quantification of the sugar types in glycoproteins. A further application provided by the present invention is highly sensitive oligosaccharide "mapping" of carbohydrates from glycoproteins or other macromolecules. Treatment of a macromolecule with known enzymes (glycosidases) will selectively generate a reproducible mixture of oligosaccharides useful in characterizing the structure and function of the macromolecule. Glycosidases such as endoglycosidase H, N-glycanase or glycopeptidase F may be useful for oligosaccharide mapping. Furthermore, the structure and location of a particular oligosaccharide within a glycoprotein may be determined by isolating a particular peptide to which an oligosaccharide is linked. The structure of the oligosaccharide may then be precisely determined by employing a combination of different enzymes or hydrolysis treatments which release reproducible, overlapping sets of short saccharides. The amino sugars may be mapped and distinguished from non-amino sugars. One skilled in the art can readily design new variations and uses for the present reagents which will push back our understanding of the structure of biological macromolecules. The present invention greatly facilitates such detailed analyses, since only minute amounts of a purified macromolecule, or a portion thereof, may be available and the present invention provides detection of exceedingly small amounts of material. For example, using a simple mixture of three common monosaccharides, $2.3\times10^{-18}$ mole mannose, $1.3\times10^{-18}$ mole glucose and $5\times10^{-19}$ mole galactose have been detected using the techniques of the present invention.

The detection methodology reported here is several orders of magnitude more sensitive than the best previously reported results with liquid chromatography or capillary electrophoresis. UV, convention fluorescence, or amperometric detection techniques which are typically used with such separation methods usually feature detection limits at picomole levels. The high sensitivity of measurements reported here are mainly due to the use of present fluorogenic reagents which are compatible with the spectral characteristics of either the helium-cadmium or argon laser. However, use of improved separation procedures such as capillary electrophoresis or, preferably, capillary zone electrophoresis, electrokinetic capillary chromatography or micellar electrokinetic capillary chromatography, enhances the resolution of mixtures of derivatized products and optimizes the detection by the procedures of the present invention. Even without buffer optimization, large numbers of theoretical plates are readily achieved (100,000 to 400,000 theoretical plates per meter) with capillary zone electrophoresis.

Separation of complex peptide mixtures by capillary zone electrophoresis has been demonstrated (Jorganson, et al., 1981, Anal. Chem. 53:1298; Jorgenson, et al., 1981, J. High Resolut. Chromatogr. Commun. 4:230. While migration rates of various peptides and other molecules can be optimized through an appropriate pH adjustment, the use of electrokinetic capillary chromatography can be beneficial in separating substances with similar net charge values. As a modified version of capillary zone electrophoresis, electrokinetic capillary chromatography introduces additional separation mechanisms to supplement the differences in electrophoretic mobilities of analytes. Through the addition of micelle-forming surfactants or inclusion-forming compounds to the buffer medium, a dynamic partition mechanism of solute separation is established. Thus, electrokinetic capillary chromatography incorporates aspects of both electrophoretic and chromatographic separation, so that subtle differences in the size, shape, hydrophobicity and charge of analytes can be exploited. Although electrokinetic capillary chromatography was originally introduced to allow for the separation of neutral compounds, this technique has also been applied successfully to the separation of various charged species.

The present invention provides improved buffers which greatly enhance separation of structurally similar amino acids, amino sugars, peptides and oligosaccharides by micellar electrokinetic capillary electrophoresis. Incorporation of anionic or cationic surfactants such as sodium dodecyl sulfate (SDS) or dodecyltrimethylammonium bromide (DTAB) and hexadecyltrimethylammonium bromide (HTAB) provide micelle-forming surfactants. Cyclodextrins provide inclusion-forming compounds.

Cationic surfactants such as DTAB or HTAB generate a micellar solution which is electrosmotically driven towards the positive electrode. Therefore, substances possessing a negative charge are accelerated in the direction of the electroosmotic flow, while positively charged species tend to migrate in the opposite direction, but are eventually overcome by the stronger electroosmotic flow. The distribution of solutes between the buffer medium and the pseudostationary micellar phase provides the needed separation selectivity. The extent of interaction with the micellar phase depends on the charge, size and hydrophobicity of the solute.

According to the present invention, cyclodextrin has been found to increase the fluorescence and improve the separation of derivatized peptides. Cyclodextrins may augment the separation of specific ranges of similarly sized and/or shaped species by selective retention of subsets of species. The excellent separation properties of cyclodextrin may also be caused by decreased diffusion coefficients due to the formation of aggregates, or by protection from adsorption to the capillary wall.

Hence, the present invention provides methods for detection of amino acids, peptides, proteins, pharmaceuticals, amino sugars, non-amino sugars and complex carbohydrates, as well as for detection of sugar moieties within glycoproteins and any other primary amine bearing molecule. Furthermore, the present invention provides techniques for detection of any molecule to which a primary amine may be attached, and for improved separation techniques for XArQCA derivatized products.

The following Examples serve to further illustrate the invention.

EXAMPLE 1

Materials and Methods

Apparatus

Figure 1:
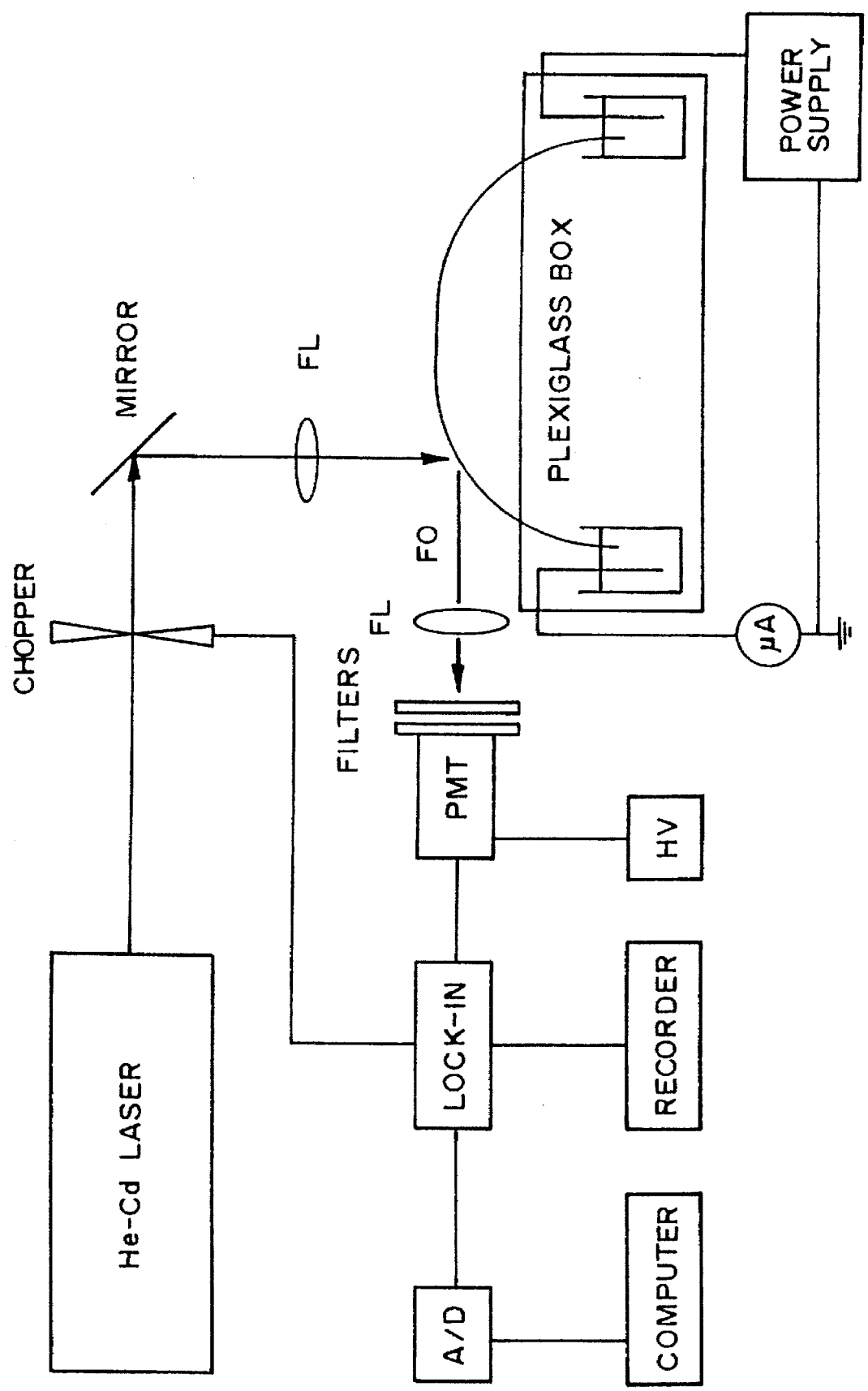
FIG. 1 depicts a schematic diagram of a capillary electrophoresis/laser-induced fluorescence detection system. FL, focal lens; FO, fiber optic; PMT, photomultiplier tube; HV, high-voltage supply.

All measurements were taken using an electrophoresis/laser-induced fluorescence detection system like that depicted in FIG. 1. Fused silica capillaries (Polymicro Technologies, Phoenix, Ariz.) of 50–100 cm in length (with 50 μm i.d., 187 μm o.d.) were suspended between two electrodes immersed in the reservoirs filled with an appropriate operating buffer solution. The high-voltage DC power supply (Spellman High Voltage Electronics Corp., Plainview, N.Y.) used is capable of delivering 0–60 kV. A plexiglas box with an interlock system provided safety for the operator.

On-column fluorescence detection was carried out by utilizing an argon or helium-cadmium laser (Omnichrome, Chino, Calif.) as a light source. An on-column optical cell was made by removing the polyimide coating from a short section of the fused silica capillary. The incident laser beam is aligned to its optimum position by adjusting the position of collecting optics between the flow cell and the detector. Therefore, the image of the flow cell can be focused on the entry slit of a monochromator. Fluorescence emission was collected through a fiber-optic placed at a right angle to the incident laser beam. Signals isolated by a band-pass filter were monitored with a R928 photomultiplier tube and amplified with a Model 128A lock-in amplifier (EG & G Princeton applied Research, Princeton, N.J.).

Static fluorescence spectral data were recorded on a Perkin-Elmer (Norwalk, Conn.) 650 spectrofluorimeter equipped with a zenon arclamp, powered by a Perkin-Elmer 150 power supply.

Synthesis of 3-(4-Carboxybenzoyl)-2-Quinolinecarboxaldehyde (CBQCA)

The synthesis of CBQCA is outlined in the Detailed Description of the Invention; specific reaction conditions are provided below. Making (4-Cyanobenzoyl)Acetone (3):

To 20 mmol sodium hydride (obtained by washing 950 mg of a commercial 50% slurry with pentane) in 7 ml THF (distilled from LiAlH$_4$) was added 1.51 g (9.37 mmol) methyl 4-cyanobenzoate (Aldrich, Milwaukee, Wis.) in 10 ml THF, followed, dropwise, by 1.38 ml (1.09 g, 18.8 mmol) acetone (distilled from CaCl2). The mixture was heated under reflux for 1.5 hours, cooled, and acidified with 3M HCl. The organic layer was washed with brine and NaHCO$_3$ and dried (MgSO$_4$). Removal of solvent left 1.116 g (6.21 mmol, 66%) (4-cyanobenzoyl)acetone.

Making 3-(4-Cyanobenzoyl)-2-Methylquinoline (4):

A mixture of 433 mg (2.32 mmol) (3), 486 mg (2.32 mmol) 2-amino-N-(p-tolyl)benzaldimine (7), 69 mL piperidine, and 9 mL 95% ethanol was heated 18 hours under reflux. Volatiles were removed by steam distillation and the residue divided between water and CH$_2$Cl$_2$. Concentration of the dried organic layer yielded 547 mg, 2.01 mmol, 87%. Making 3-(4-Carboxybenzoyl)-2-Methylquinoline (5a):

To 547 mg (2.01 mmol) 4 suspended in 13 mL 95% ethanol was added 500 mg KOH. The mixture was heated under reflux 6 hours, cooled, and concentrated. The residue was divided between ether and water and the aqueous portion acidified to pH 5 with tartaric acid, digested 15 min, and filtered. The precipitate was washed with water and dried in vacuo, yielding 266 mg, 0.914 mmol, 45%.

Making 3-(4-Carboxybenzoyl)-2-Quinolinecarboxaldehyde (CBQCA) (preferred reagent A):

To a solution of 266 mg (0.914 mmol) 5a in 6 ml acetic acid was added 112 mg (1.01) mmol selenium dioxide. The mixture was stirred at 80° C. for 2 hours and filtered through Celite. The precipitate, largely selenium, was washed with several portions of hot methanol. Product was isolated by dilution of the filtrate with water, digestion, filtration, washing with water, and drying in vacuo. The yield was nearly quantitative.

Synthesis of Substituted 3-(2-Furoyl)Quinoline-2-Carbaldehyde (FQCA) Reagents.

Conditions appropriate for synthesis of unsubstituted FQCA, are presented below. To synthesize substituted FQCA reagents starting materials are chosen which have the appropriate R or X substitutions.

N-(p-Tolyl)-o-nitrobenzaldimine: A mixture of 9.68g (90.5 mmol) p-toluidine and 10.89 g (72.1 mmol) o-nitrobenzaldehyde in 25 ml ethanol was kept at 25° C. The precipitate, which began to form after 5 min, was collected on a filter, washed with cold ethanol, and air-dried. Additional precipitate was obtained by dilution of the filtrate with water and refrigeration. A yield of 16.0 g, 66.7 mmol (93%) was obtained.

N-(p-Tolyl)-o-aminobenzaldehyde: To a solution of 16.0 g, (66.7 mmol) N-(p-tolyl)-o-nitrobenzaldimine in 33 ml 95% ethanol at reflux temperature was added a solution of 31 g (129 mmol) $Na_2S$-$9H_2O$ in 30 ml 50% aqueous ethanol over 15 min, so as to maintain reflux. The mixture was heated under reflux an additional 15 min and cooled to effect crystallization. Solid was collected on a filter, washed with water, and air-dried, yielding 4.09 g (19.5 mmol, 29%) N-(p-tolyl-o-aminobenzaldehyde. No attempt was made to secure additional product from the filtrate.

(2-Furoyl)acetone: 4.27 ml (5.04 g, 40 mmol) methyl 2-furoate was added to a suspension of NaH (made from 3.83 g commercial NaH slurry by removal of the mineral oil with pentane) in 30 ml anhydrous diethyl ether. To this was added, so as to maintain the temperature below 30° C., 5.87 ml (4.64 g, 80 mmol) acetone (dried over $CaCl_2$). This mixture was heated under reflux for 2 h, cooled, and divided between diethyl ether and 3M HCl. The ether layer was washed with brine, dried ($MgSO_4$), and concentrated to yield 6.06 g of a red oil (raw yield 99%) which was purified by vacuum distillation (b.p. 85°–90° C./1 torr).

3-(2-Furoyl)-2-methylquinoline: A solution of 410 mg (1.95 mmol) N-(p-tolyl)-o-aminobenzaldehyde 326 mg (2.15 mmol), (2-furoyl)acetone and 50 mg piperidine in 4 ml 95% ethanol was heated overnight under reflux. Removal of he volatile materials left a black, gummy oil which was taken up in dichloromethane and, after being washed with 3M NaOH, brine, and dried ($MgSO_4$), purified by flash chromatography [eluent, 3:2 pentane-diethyl ether (3:2)] yielding 355 mg (1.50 mmol, 77%) product.

3-(2-Furoyl)quinoline-2-carbaldehyde: A mixture of 355 mg (1.50 mmol) 3-(2-furoyl)-2-methylquinoline and 183 mg (1.65 mmol) $SeO_2$ in 6 ml acetic acid was heated for 17 h in an 80° C. bath. The solvent was removed by rotary evaporation. The dichloromethane extract of the residue was washed with 1M NaOH and brine and dried ($MgSO_4$). Concentration yielded 284 mg oil, 1.13 mmol, 75% raw. The ultimate purification was done by liquid chromatography.

Derivatization Procedure

XArQCA reagent solutions were prepared by dissolving reagent in methanol (3 mg/ml). Potassium cyanide was dissolved in water to give a 10 mM solution. Derivatization was carried out by mixing an aliquot with 10–20 μl of potassium cyanide solution, and 5–10 μl of XArQCA solution. The mixture was then allowed to stand at room temperature for about one hour prior to the sample injection into a capillary analytical system. Aliquots of protein or polysaccharide hydrolysates or glycoprotein-derived oligosaccharide and tryptic digest solutions were derivatized in the same manner as smaller molecules such as amino acids, amino sugars and peptides. The samples were introduced into the capillary analytical system by either a hydrodynamic or electromigration technique. Other proteins can be hydrolyzed by these, and other procedures.

Protein Hydrolysis

Lysozyme was acid-hydrolyzed in a 1-ml vacuum hydrolysis tube (Pierce Chemical, Rockford, Ill.) for 24 hours at 110° C. The solution was subsequently lyophilized and the residue dissolved in water just prior to derivatization.

Tryptic digestion of β-casein was done using a small column of an enzyme immobilized on the agarose gel, as described recently by this laboratory (Cobb et al., 1989, Anal. Chem. 61:2226–2231).

Partial Hydrolysis of Polysaccharides

Procedure 1: Approximately 10 mg of a polysaccharide sample was dissolved in 1% acetic acid and hydrolyzed with an excess of concentrated hydrochloric acid. A portion of this solution was introduced into a screw-cap vial and put on a thermostatted heat block at 80° C. for 24 hours. After the completion of hydrolysis, 300 μl of hydrolysate was withdrawn and dried. The residue was redissolved in 100 μl of deionized water and made ready for derivatization by a fluorogenic reagent (XArQCA).

Procedure 2: 50 mg of polysaccharide was dissolved in 2 ml of deionized water and 0.5 ml of hydrochloric acid (1.0N) and heated at 100° C. 2.5 ml of concentrated hydrochloric acid was subsequently added while maintaining hydrolysis for 34 hours at 100° C. After completion, 50 μl hydrolysate was dried and redissolved in 50 μl of deionized water for a subsequent derivatization by a XArQCA reagent.

Release and Detection of Sugars from Glycoproteins and Oligosaccharides

The procedures were carried out with either trifluoroacetic acid or hydrochloric acid as described by Honda and his co-workers (Honda et al., 1984, Anal. Chem. 142:167–174; Honda et al, 1989, Anal. Biochem 180:351–357). A portion of the glycoprotein or oligosaccharide solution dissolved in water (20 μg/l) was mixed with 4.0M hydrochloric acid (200μl) in a screw-cap vial. The vial was closed tightly and placed into a heating block at 100° C. for 6 hours. This treatment releases all sugars. To release non-amino sugars, with some amino sugars, another portion of sample solution can be hydrolyzed by 2.0M trifluoroacetic acid at 100° C. for 6 hours. After hydrolysis, the reaction mixtures were cooled and the acid removed by evaporating the solution to dryness under either nitrogen stream or reduced pressure. Residues were redissolved in water and stored for further treatment.

To detect the endogenous amino sugars, a portion of an HCl hydrolyzed sample was deionized by passing it through a small column of Amberlite IRA-900 anion exchanger, and the collected eluate was dried and redissolved in a small volume of water for XArQCA derivatization of amino sugars.

To allow separate detection of the endogeneous non-amino sugars, the endogenous amino sugars were acetylated to block derivatization with the present XArQCA reagents. Therefore, a portion of hydrolyzed sample was dissolved in a saturated aqueous solution of sodium bicarbonate (100–500 μl, depending on the sample concentration) and acetic anhydride (50–200 μl) for reacetylation of the amino groups of the amino sugars released from glycoproteins or oligosaccharides. The mixture was allowed to stand at room temperature overnight and deionized by passing it through Amberlite IRA-900 (anion exchanger) and Amberlite 200 (cation exchanger) columns. The sample was evaporated to dryness and redissolved in water for reductive amination.

Preparation of Glycoprotein-Derived Oligosaccharides.

To obtain larger oligosaccharides, as opposed to sugars, a glycoprotein may be treated with glycosidases or hydrazine. Glycosidase treatment is done under the enzyme conditions specified by the manufacturer, followed by isolation of the oligosaccharides. To treat with hydrazine 10 mg amounts of a glycoprotein were introduced into a screw-cap vial, and a minimum of anhydrous hydrazine (Pierce, Rockford, Ill.) was added to cover the sample. The closed vial was heated at 100° C. for 12 hours. After removing hydrazine under a stream of nitrogen, the vial was placed overnight in a desiccator containing sulfuric acid. The presence of carbohydrates in samples was verified by 13C-NMR runs using Model AM-500 (Bruker, Karlsruhe, FRG). The cleaved carbohydrates were subsequently isolated by a Bio-Gel P-2 (Bio-Rad, Richmond, Calif.) chromatography. Using water as the mobile phase, the carbohydrate fraction was collected and dried.

Acetylation of Glycoprotein-Derived Oligosaccharides

As described above, acetylation blocks endogenous amino groups so will not react with the present XArQCA reagents, allowing endogenous non-amino sugars to be distinguished from endogenous amino sugars.

The dried oligosaccharides were redissolved in water and a portion of this solution was subjected to reacetylation of the amino groups on the oligosaccharide chains by adding 200–500 µl of saturated sodium bicarbonate solution and 50–200 µl of acetic anhydride and letting the mixture stand at room temperature overnight. The solution was then deionized by both an Amerlite IRA-900 anion exchanger and an Amberlite 200 cation exchanger (Sigma, St. Louis, Mo.). The collected solution was freeze-dried and redissolved in water for further treatment.

Reductive Amination of Neutral Carbohydrates

Standards of mono- and oligosaccharides (reducing carbohydrates), and the samples obtained from cleavages of glycoproteins were dissolved in water and placed in screw-cap vials or polypropylene plastic sample vials. Excess 2.0M ammonium sulfate or 4.0M ammonium chloride and 0.4M sodium cyanoborohydride were added into the vials and mixed well. The tightly sealed vials were placed into a heating block at 100° C. for 100–120 minutes. After the completion of reaction, the solutions were immediately cooled by putting the vials into an ice-bath. Such mixtures can either be used directly for derivatization by a XArQCA reagent, or dried and redissolved.

The identity of the reductive amination product was verified by $^{13}$C-NMR with Model Am-500 (Bruker, Karlsruhe, FRG). The chemical shift of the carbon at the reducing end becomes δ-42 ppm after the introduction of the primary amine group, when compared with the original value of δ-98 ppm. No signal was observed around δ-98-102 ppm, where the 1'-carbon of the pyranose structure would appear if the reactions were not completed.

EXAMPLE 2

Optimum Reaction Conditions for Derivatization

The reaction scheme for derivatizing amino acids with CBQCA is given below:

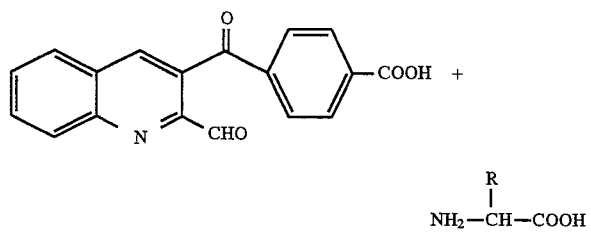

3-(4-Carboxybenzoyl)-2-quinolinecarboxaldehyde

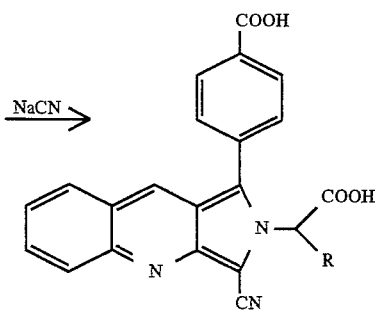

Figure 2A:
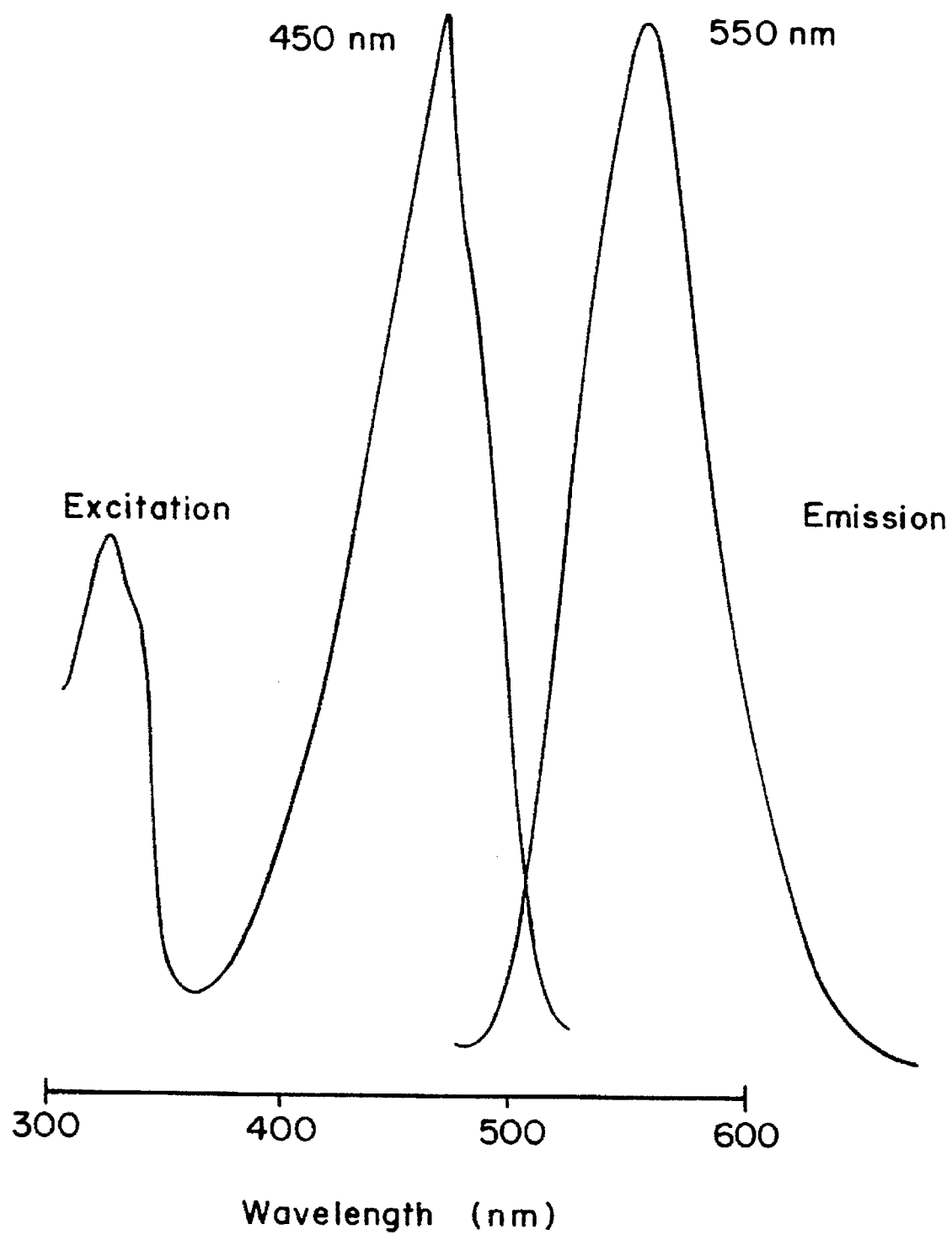
FIG. 2A depicts the wavelength of maximal excitation (CBQCA) derivatized glycine and emission of 3-(4-carboxybenzoyl)-2-quinolinecarboxaldehyde (CBQCA) derivatized glycine.
Figure 2B:
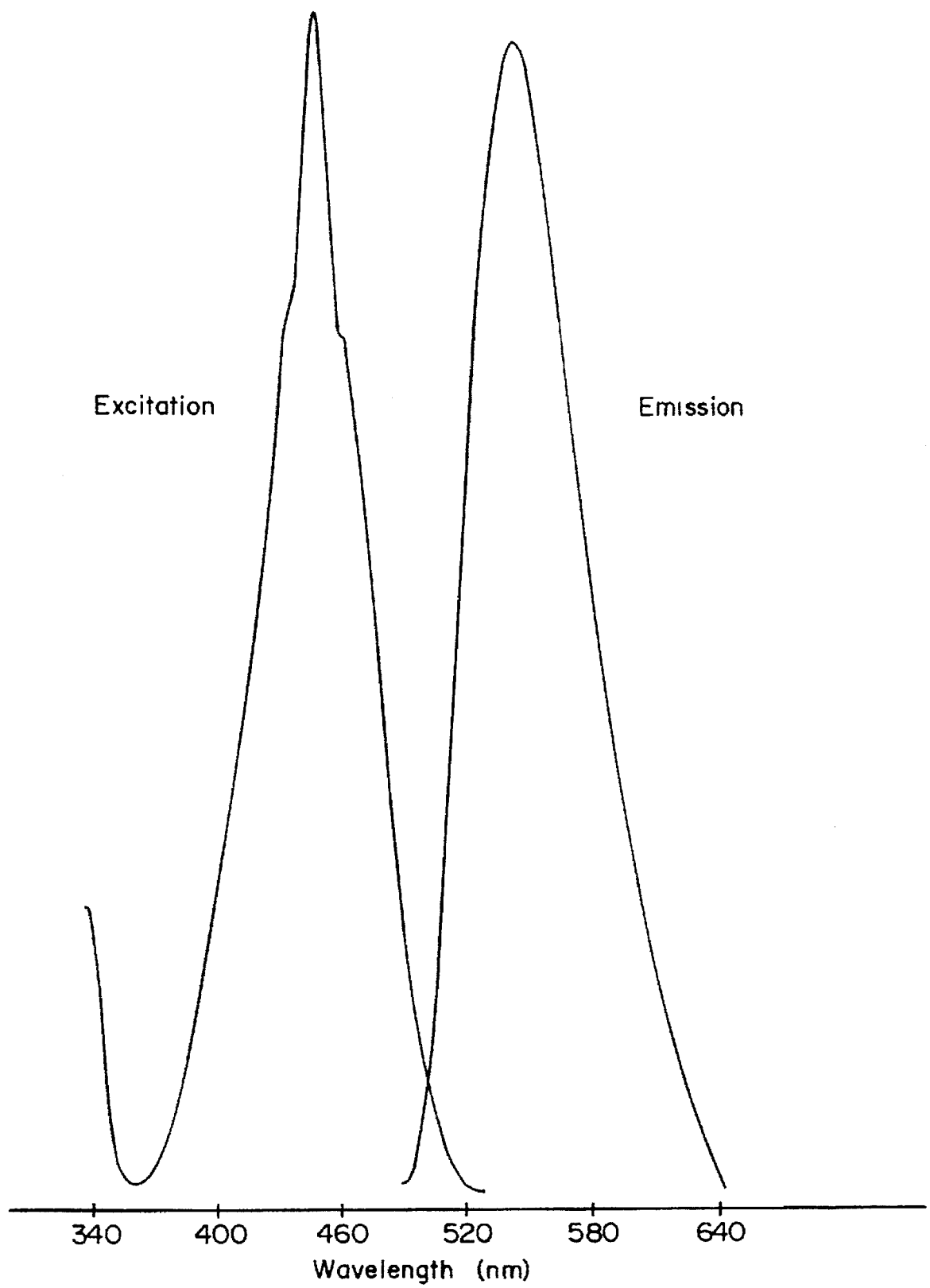
FIG. 2B depicts the wavelength of maximal excitation and emission of CBQCA derivatized D(+)-galactosamine. Excitation maximum: 456 nm. Emission maximum: 552 nm.

All primary amino acids tested react readily, under similar conditions, with CBQCA reagent. The excitation and emission spectra for a CBQCA-amino acid derivative are shown in FIG. 2A. The excitation maximum for the glycine derivative has been found at 450 nm, which closely matches the He-Cd laser 442-nm laser line. Its emission maximum is at 550 nm. The excitation and emission spectra for CBQCA-D (+)-galactosamine are shown in FIG. 2B. The observed excitation maximum is 456 nm, and the emitted light can be measured near 552 nm. A surprising and highly useful finding of the present invention is that the present XArQCA reagents react easily with various peptides which do not react readily with previously used aroylaraldehydes reagents. This is most likely due to the presence of an ionic moiety in the XArQCA reagents and improved "phase transfer" during derivatization.

Amino acids, amino sugars and small peptides were used as model systems to assess the effects of reagent concentration, cyanide concentration and pH upon the derivatization reaction. With model amino acids, a minimum 6 fold molar excess of a XArQCA reagent and a 5-fold molar excess of the cyanide catalyst was found to be preferable.

Figure 3:
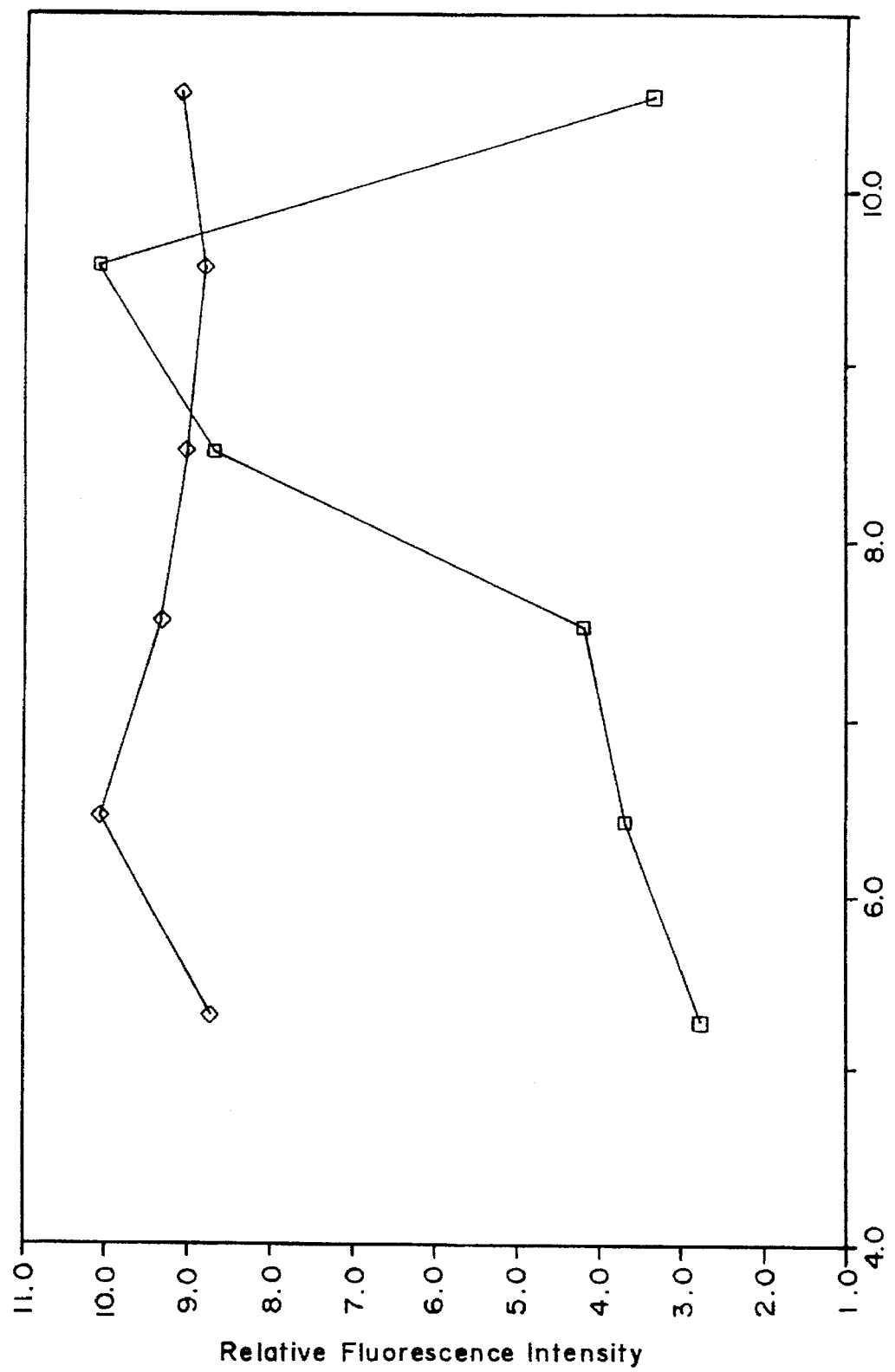
FIG. 3 depicts the effect of pH on the yield of CBQCA-derivatized peptides.

A representative result of the effect of pH on the derivatization of two peptides is shown in FIG. 3. A small peptide (Gly-Gly-Tyr-Arg) shows a distinct optimum pH of around 8.5 to 9.5, which is also the range for the amino acid maximum fluorescence intensity. While the larger peptides, such as Des-Asp$^1$-angiotensin I (a nine-residue peptide), react well with CBQCA, no distinct reaction optimum is indicated (FIG. 3). Hence, the pH optimum for XArQCA derivatization of amino acids and peptides is about pH 9.0.

The analytically satisfactory stability of the formed isoindoles and reaction reproducibility were assessed for several types of primary amines. FIG. 4 depicts the stability of CBQCA-derivatized D(+)-galactosamine. After 10 hours at room temperature no measurable loss of fluorescent signal was observed. Also shown in FIG. 4 is the time (about 40 min. at room temperature) required for optimum reaction of CBQCA with galactosamine. The derivatized products can also be evaporated to dryness and kept in freezer for later use.

Factors affecting the derivatization of amino sugars were also assessed. Investigations of optimum pH conditions indicated the value of 7.0, which is different from the reaction between the amino acids and CBQCA (pH 9.0), is preferable. The effects of molar excess of the CBQCA reagent and the cyanide catalyst are depicted in FIG. 5. One to two-fold molar excess of CBQCA and one to three-fold molar excess of cyanide were found adequate for achieving maximum reaction yield. At higher concentration of either the reagent or catalyst, fluorescence yields decreased appreciably. Therefore, one to two-fold molar excess of an XArQCA reagent and one to three-fold molar excess of cyanide are preferred.

EXAMPLE 3

Separation and Detection

Amino Acids

In previous work on capillary electrophoresis of amino acids, difficulties were encountered in resolving all constituents (Gordon et al., 1988, Science 242:224–228; Nickerson et al., 1988, J. High Resolut. Chromatagr. Commun. 11:533–534; and Chung et al., 1988. Science 242:562–564). Therefore, this problem was further investigated in accordance with the present invention. Initial investigations demonstrated that capillary zone electrophoresis in various buffer media was successful in resolving roughly one-half of the seventeen CBQCA-derivatized amino acids. Addition of sodium dodecyl sulfate (SDS) improved this separation considerably (FIG. 6). In FIG. 6 the individual peaks represented 9 femtomoles of each amino acid. From the primary amino acids that are commonly encountered in proteins, only lysine was missing in FIG. 6 due to double-tagging by CBQCA which leads to spectroscopic and possible fluorescence quenching problems (De Montigny et al., 1987; Anal. Chem. 59:1096–1101; Matuszeqski et al., 1987, Anal. Chem. 59:1102–1105). The lysine problem can potentially be overcome if the amino side chain is blocked by methylation prior to hydrolysis of the protein sample. However, this procedure will not allow the N-terminal amino acid to be XArQCA derivatized after the acid hydrolysis of a protein. Therefore, methylated and unmethylated protein samples may be hydrolyzed and derivatized to allow lysine detection.

Detection limits for the individual amino acids represented in FIG. 6 have been assessed in the range of 20 to 70 attomoles (signal-to-noise ratio equal to 3) with the exception of CBQCA-glycine which had a minimum detectable quantity of 1.4 attomoles (0.2 nanoliter of $7 \times 10^{-9}$M solution injected). The linear dynamic range for these measurements has been assessed at over three orders of magnitude.

FIG. 7 demonstrates separation of the amino acids obtained from hydrolysis of a 15 ng amount of lysozyme. It should be emphasized that while this minute quantity of the protein was initially subjected to hydrolysis and subsequent derivatization with CBQCA, FIG. 7 represents a considerably smaller aliquot of the analyzed solution (1.9 pg, or 134 attomoles of lysozyme).

Separation of CBQCA-Derivatized Peptides

Initially, standard solutions of small (3 to 4 residue) peptides and somewhat larger angiotensin derivatives were tagged with CBQCA and separated. In a pH 9.50 borate buffer, the negatively charged peptide derivatives migrated in the system according to their predicted mass-to-charge ratios, although the presence of electroosmotic flow (Jorgensen et al., 1981, Anal. Chem. 53:1298–1302) modified their migration rates somewhat. An electropherogram of 10 model peptides, separated in 15 min., is shown in FIG. 8; since none of these standards contained lysine in their molecules, single peaks were observed. Although CBQCA was also found to react with proteins, formation of multiple peaks diminishes the value of protein derivatization followed by hydrolysis and amino acid detection.

Detection limits for the model peptides, Val-Ala-Ala-Phe and Gly-Gly Tyr-Arg were assessed at 4.6 and $13.8 \times 10^{-18}$, respectively. Plotting peak heights against concentration of peptides derivatives ($10^{-8}$ to $10^{-5}$M), the linear dynamic range was found to be at least four orders of magnitude; for example, the correlation coefficients for Gly-Leu-Tyr and Gly-Gly-Tyr-Arg were 0.9956 and 0.9984, respectively. During the peptide separations and sensitivity studies, 20 mM-cyclodextrin was used as a buffer additive. This addition resulted in a several fold increase of detection sensitivity and narrower peptide peaks.

Following the encouraging results on the standard peptide mixtures, an exploration of CBQCA as a reagent for high-sensitivity peptide mapping was carried out. FIG. 9 demonstrates a-complex electropherogram obtained from a tryptic digest of a small amount of β-casein. This recording represents just 17 femtomoles (392 pg) of the digested protein. Yet, the pattern was found highly reproducible in run-to-run and sample-to-sample comparisons.

Separation of Closely Related Amino Sugars

Figures 10A, 10B, 10C:
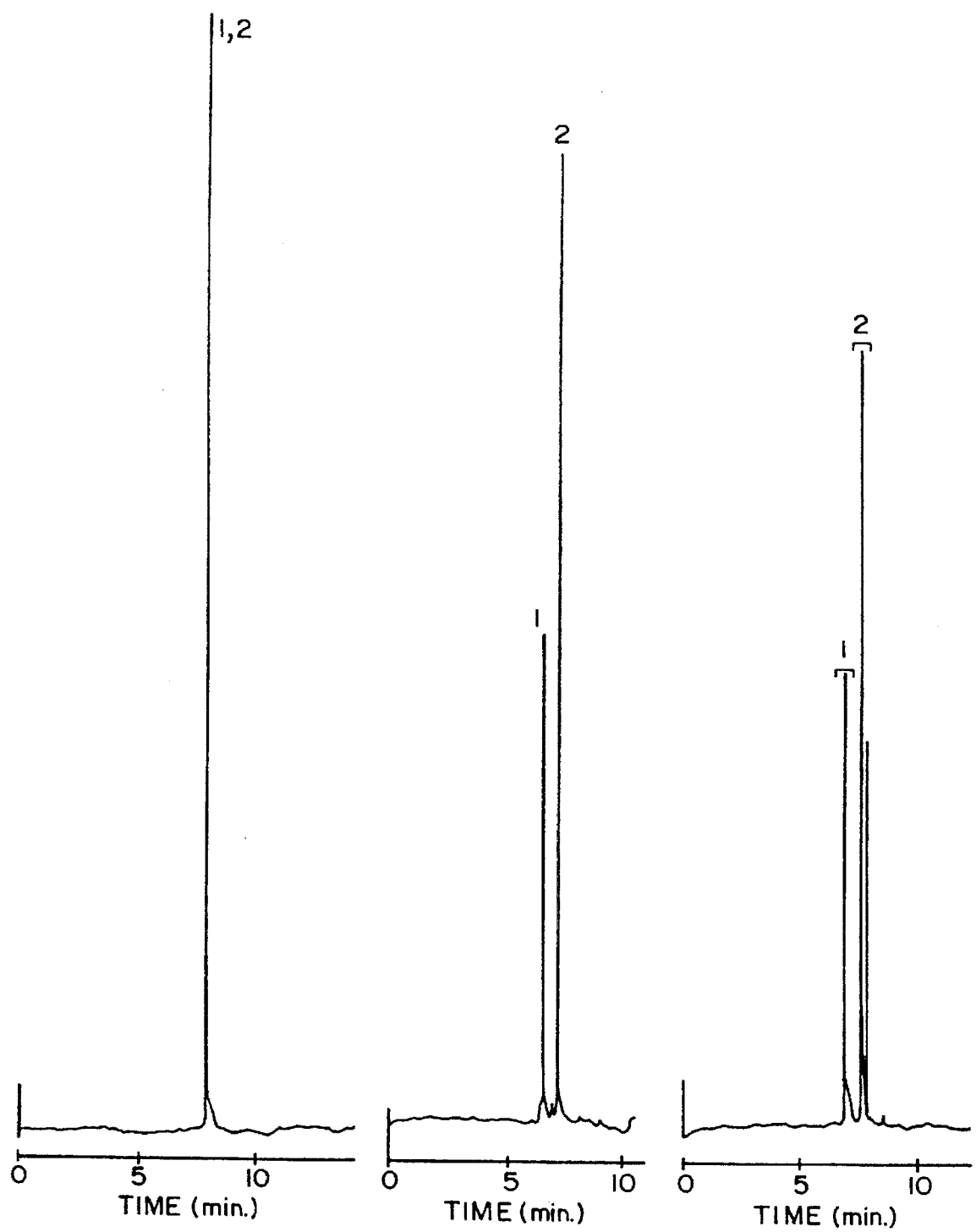

Initially, D(+)-glucosamine and D(+)-galactosamine were selected as model solutes for electrophoretic measurements (FIG. 10). These two amino sugars are structurally similar to each other (a difference in orientation of a single hydroxy group). When the negatively charged CBQCA reagent moiety is added, the electrophoretic mobilities of both derivatives were expected to be identical. As demonstrated in FIG. 10(A), there is no separation of these solutes in the phosphate buffer. However, the separation of glucosamine and galactosamine is enhanced by taking advantage of the steric difference at the 4-hydroxy group which permits a variable degree of interaction with the borate. Such an association has been studied extensively in chromatography for catechol derivatives and carbohydrates (De Jong et al., 1985, J. Chromatogr. 322:43–53; Yoshino, et al., 1979, Bull. Chem. Soc. Jpn. 52:3005–3009; and Steinberg, 1964, *Organoboron Chemistry*, Wiley-Interscience, New York: Chapter 6). More recently, this interaction was demonstrated in capillary electrophoresis of catechols (Wallingford et al., 1988, J. Chromatogr. 441:299–309). Not wishing to be so limited, the likely complexation scheme for glucosamine and galactosamine with borate is given below:

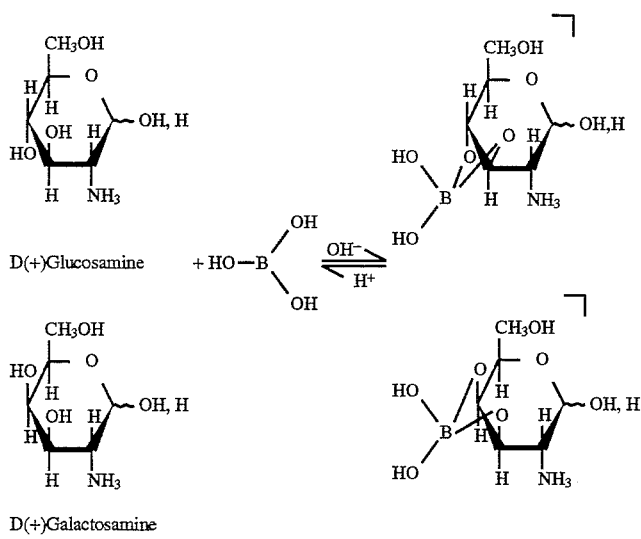

As shown in FIG. 10(B), a baseline resolution of glucosamine and galactosamine derivatives is easily achieved upon the addition of borate ion into the carrier buffer. The electropherogram shown in FIG. 10(C) was obtained with a sample solution after standing at room temperature for several days. Apparently, each peak was split into a pair. This phenomenon is probably due to the formation of the equilibrium α- and β-anomeric forms of the amino sugars. A further insight into the borate separation mechanism is given in FIG. 11, demonstrating the effect of borate concentration on resolution of the derivatized sugars. In these experiments, appropriate amounts of borate were added into the phosphate buffer solution while maintaining the buffer concentration and pH constant. Within the studied range of borate concentration (0–25 mM), migration times and resolution were determined, indicating a complete separation at 10 mM borate concentration.

Using an appropriate fluorogenic reagent for laser-induced fluorescence measurements of carbohydrates has a major advantage compared to other detection approaches to high-sensitivity measurement. The minimum detectable amount for the derivatized galactosamine was assessed at $5 \times 10^{-19}$ mole (signal-to-noise ratio equal to 3) under the present instrumental conditions.

During attempts to separate additional amino sugars of closely related structures, dramatic improvements in resolution were achieved through the use of an anionic surfactant, sodium dodecyl sulfate (SDS), as a buffer additive. Separation of a model mixture of six amino sugars is shown in FIG. 12 using SDS above its critical micelle concentration. The separation achieved here is by micellar electrokinetic chromatography (Terabe, et al., 1984, Anal. Chem. 56:111–1131 where the solute distribution occurs between the (pseudostationary) micellar phase and the phosphate/borate buffer moving toward the negatively charged electrode due to electroosmotic flow. All major peaks in FIG. 12 were verified by comparison of their electrophoretic mobilities with standards; smaller peaks are due to impurities in the standard chemicals.

Figure 13A:
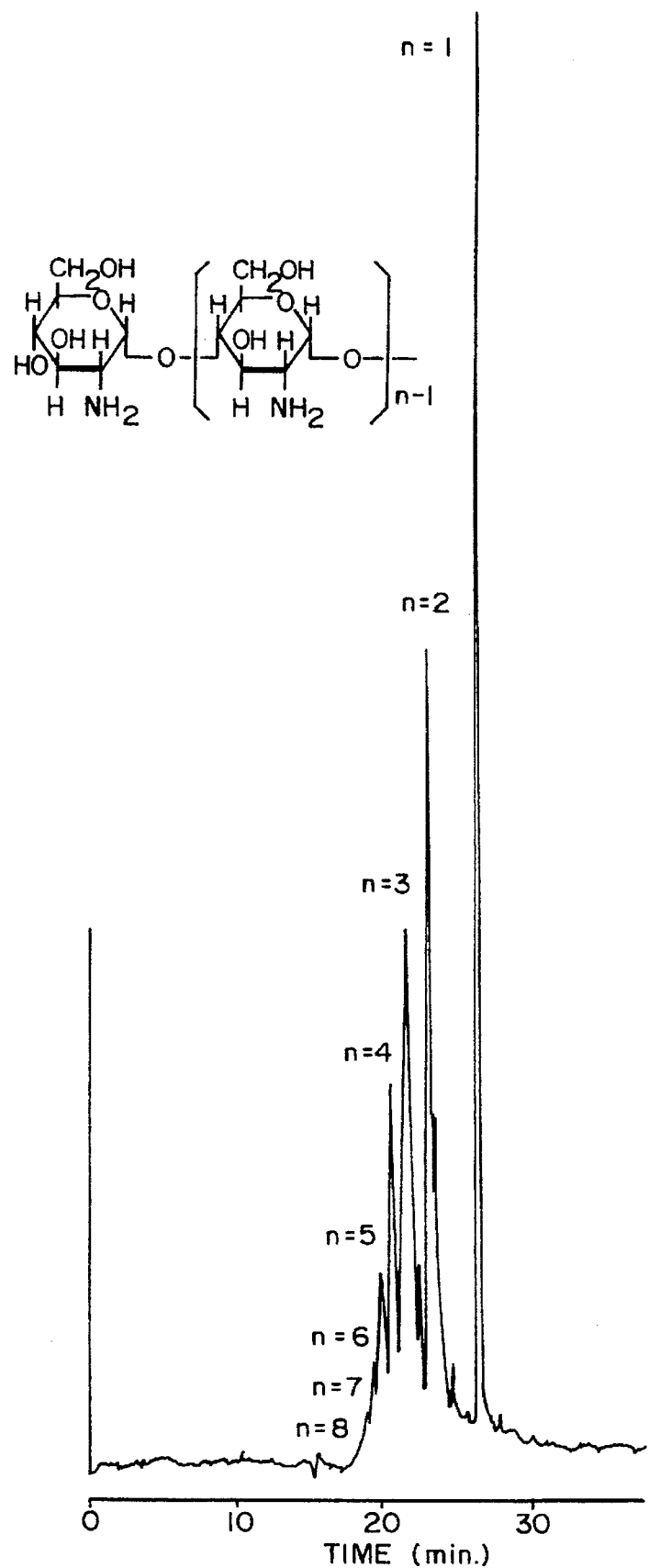
Figure 13B:
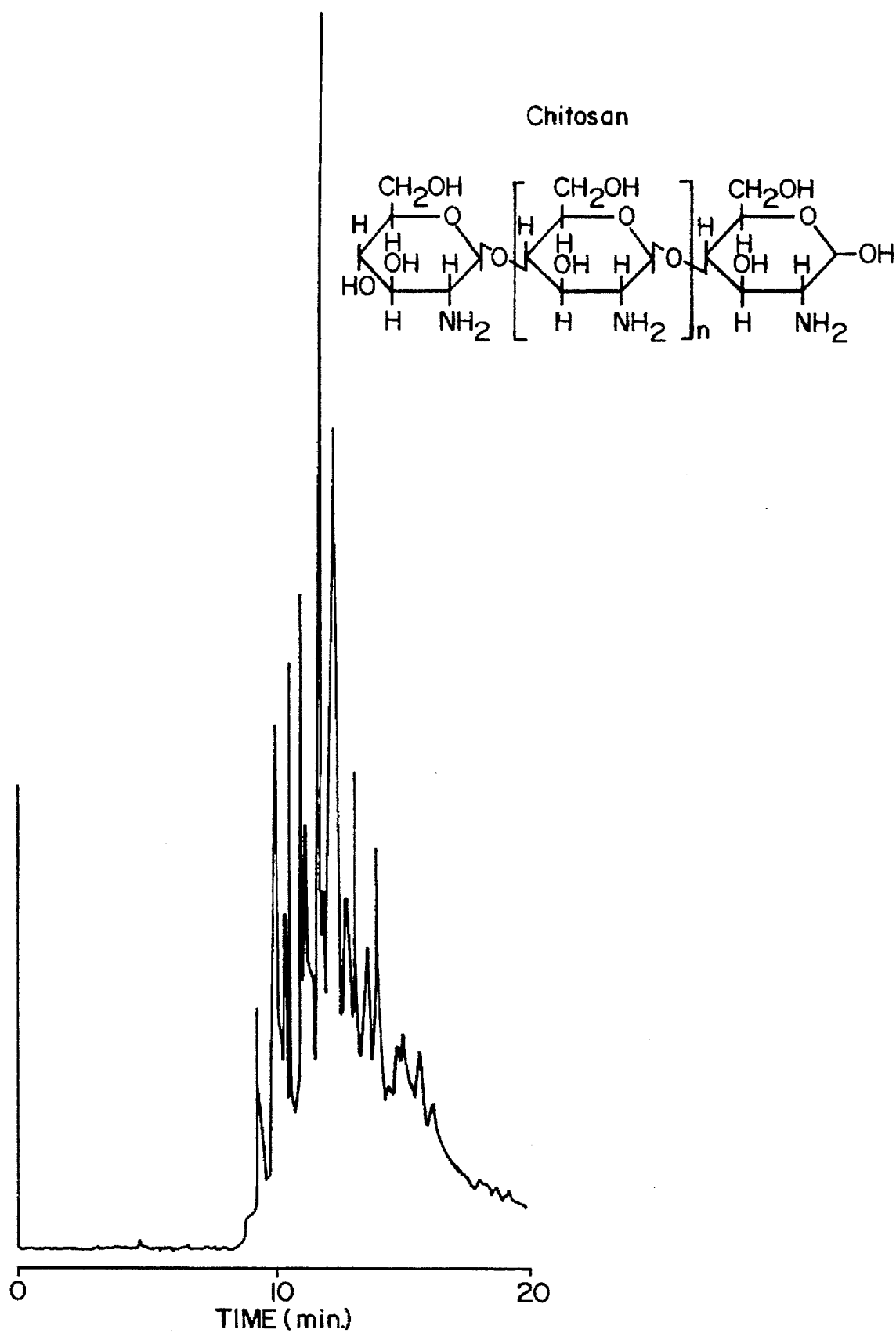
Figure 14B:
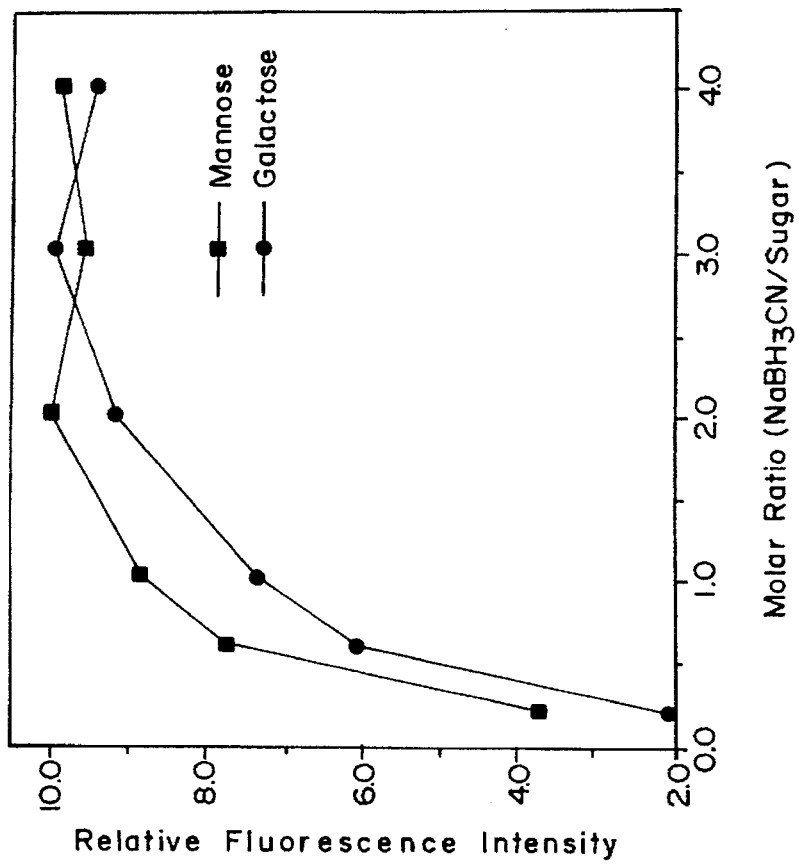
Figure 14A:
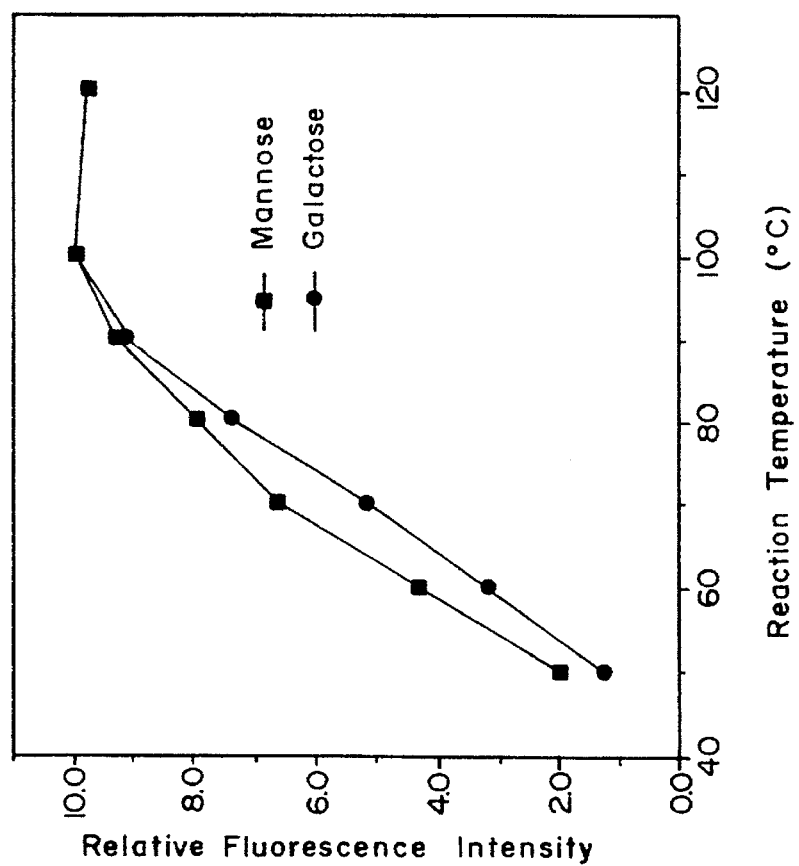
Figure 14D:
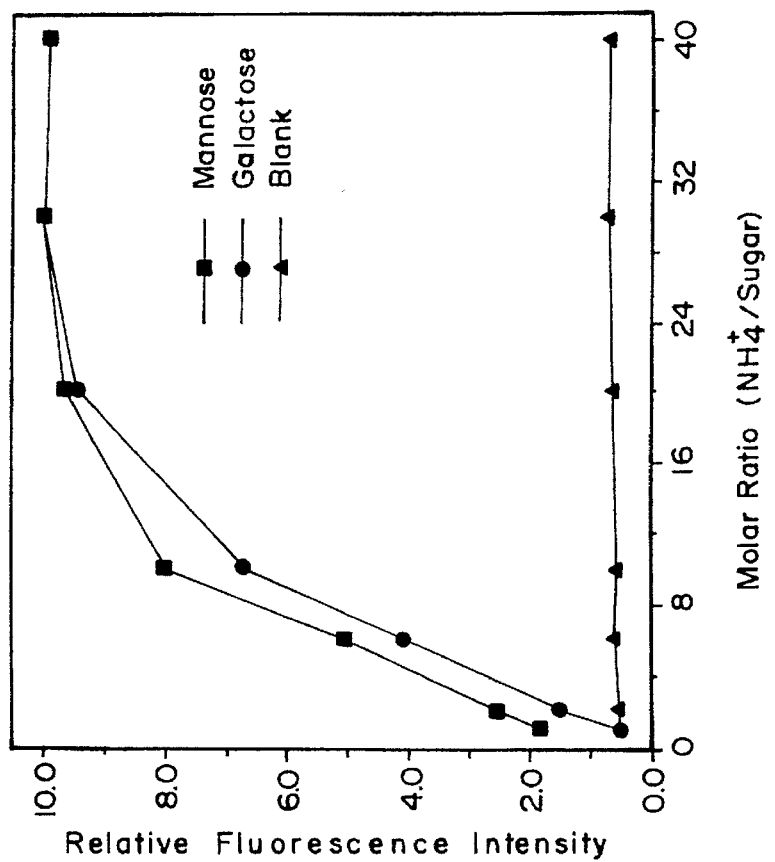
Figure 14C:
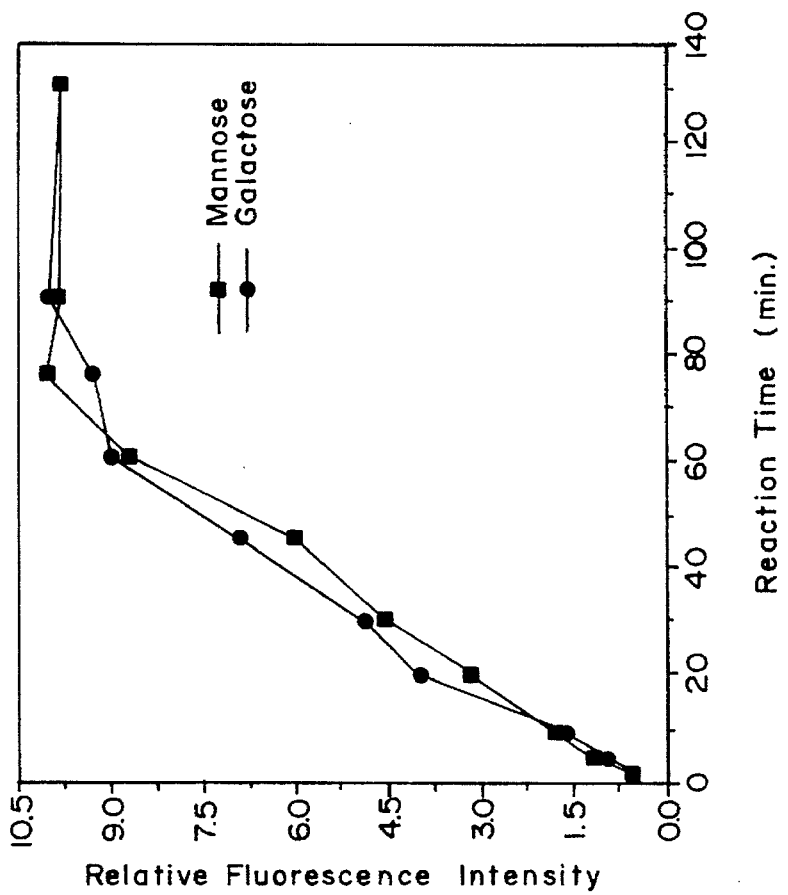

The present analytical procedures may be applied to larger carbohydrates, as is shown by separation of oligosaccharides from chitosan (N-acetylated chitin). Chitosan, a polysaccharide with the molecular weight ranging from 70,000 to 2,500,000, was hydrolyzed under acidic conditions and derivatized with CBQCA. FIG. 13 demonstrates examples of the oligosaccharide electrophoretic patterns obtained by capillary electrophoresis from the hydrolyzed sample. A sample of chitosan was hydrolzyed by concentrated hydrochloric acid at 100° C. for 34 hours, giving several peaks which represent different oligomers (FIG. 13A). FIG. 13(B) shows another electrophoretic pattern from a chitosan sample hydrolyzed under different conditions (as described in Example 1). The molecular size distribution of this chitosan hydrolytical product is not yet fully understood.

EXAMPLE 4

Detection of Carbohydrate by Amination Followed by Derivatization

Non-amino sugars may be detected according to the present invention if a primary amine group is first added to the sugar. Reductive amination is a known organic reaction but its analytical applications have been rare. Reaction of an aldehyde with ammonia in the presence of a reducing agent, sodium cyano-borohydride ($NaBH_3CN$), leads to an amine as follows.

Reductive Amination

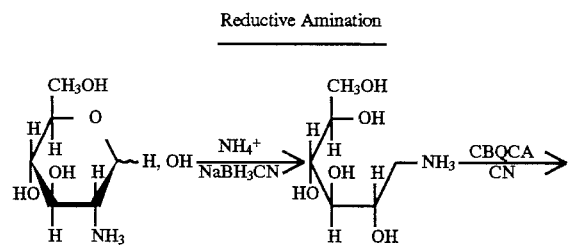

-continued
Reductive Amination

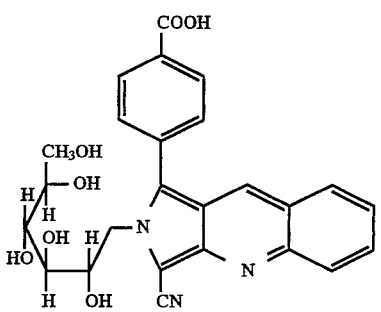

In order to achieve optimum detection sensitivity and reproducibility, reductive amination conditions were optimized with respect to reaction temperature, reaction time, and the molar ratios of the reducing agent and ammonium ion to sugars. Mannose and galactose, were two model components for these experiments. The fluorescence intensity was measured at least three times, while the entire procedure were repeated several times to insure precision.

The rate of reductive amination increases with temperature, with a maximum fluorescence intensity reached in about 100 minutes at 95° C. Accordingly, 100° C. was set as a standard for all following experiments. Stable fluorescence was observed when the molar ratio of $NaBH_3CN$ to substrate was at least 2:1, while no adverse effects were seen at significantly larger ratios. However, a large excess of ammonium ion (either from $(NH_4)_2SO_4$, $NH_4Cl$, or other ammonium salts) was needed to ensure reaction yield. Due to a concern that the large amount of ammonium salt needed might yield a side product with CBQCA, background fluorescence in the absence of sugar was checked but a negligible amount was observed. In practical measurements by chromatography electrophoresis/laser-induced fluorescence, a very small reagent peak may be found which has no adverse effects on analytical results. The results of optimization studies are summarized in FIG. 14 (A–D).

Figure 15A:
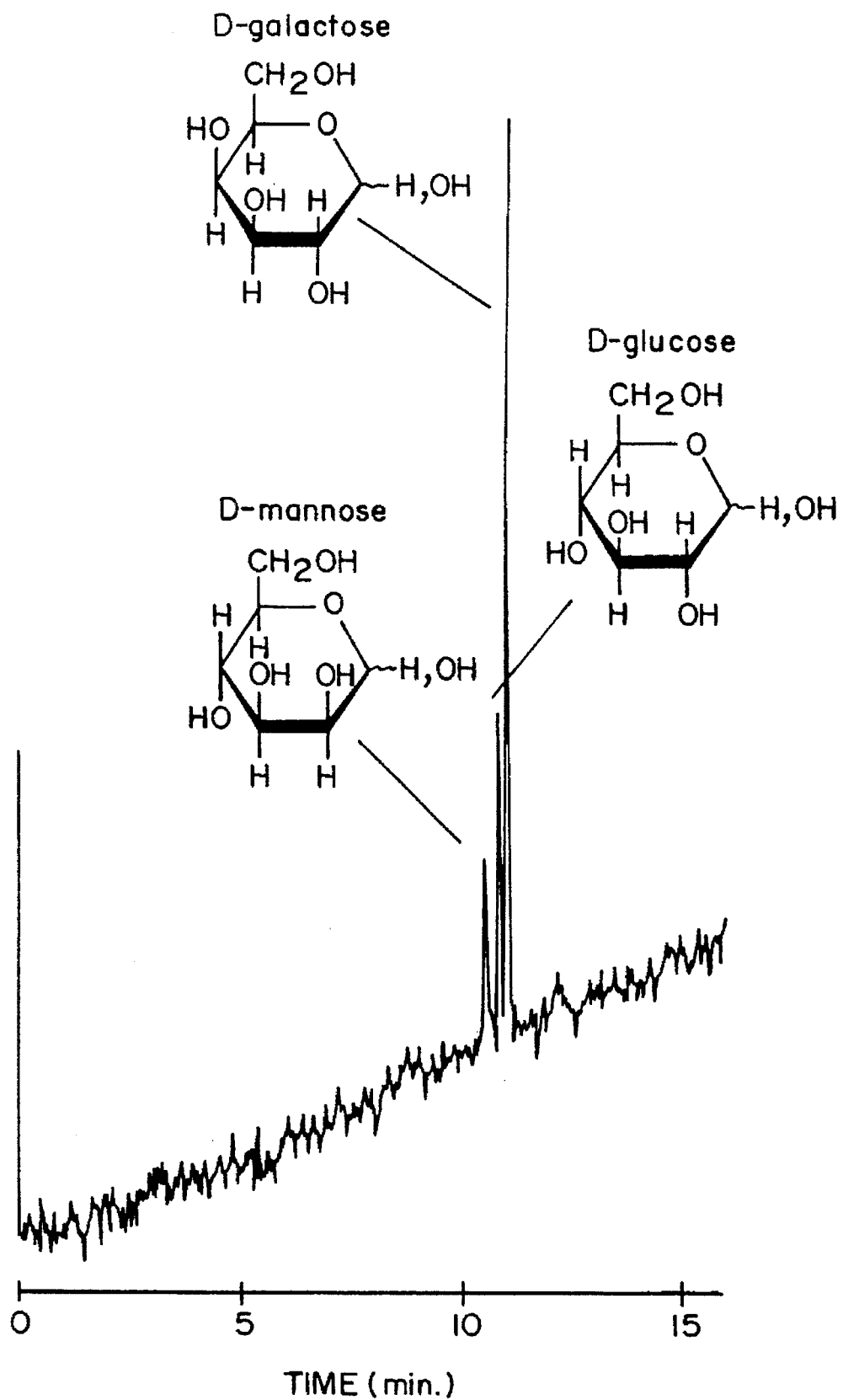

Under the optimized conditions, detection limits were examined for three most common monosaccharides (mannose, glucose, and galactose). The electromigration sample introduction was utilized to determine precisely the injection volumes. FIG. 15A shows an electropherogram of this simple mixture obtained with the solution of $3.9 \times 10^{-9}M$ concentration. With 2.1 nl sample injected, the detection limits correspond to $2.3 \times 10^{-18}$ for mannose $1.3 \times 10^{-18}$ for glucose, and $0.5 \times 10^{-18}$ for galactose (signal-to-noise ratio- 3). The relationship between the peak height and concentration of standard monosaccharides was found linear over four orders of magnitude ($10^{-9}$ to $10^{-5}M$) with satisfactory correlation coefficients ($R^2=0.998$ for all three sugars).

The detection methodology reported here is several orders of magnitude more sensitive than the best previously reported results with liquid chromatography (Hardy et al., 1988, Anal. Biochem. 170:54–62; Honda et al., 1984, Anal. Chem. 142:167–174 and Honda et al., 1989, Anal. Biochem. 180:351–357) and capillary electrophoresis (Honda et al., 1989, Anal. Chem 176:72–77). UV, conventional fluorescence, or amperometric detection used with such separation methods usually feature detection limits at picomole levels. The high sensitivity of measurements reported here is mainly due to the use of a suitable fluorogenic reagents which are compatible with the spectral characteristics of the helium-cadmium-ion or argon lasers.

Figure 15B:
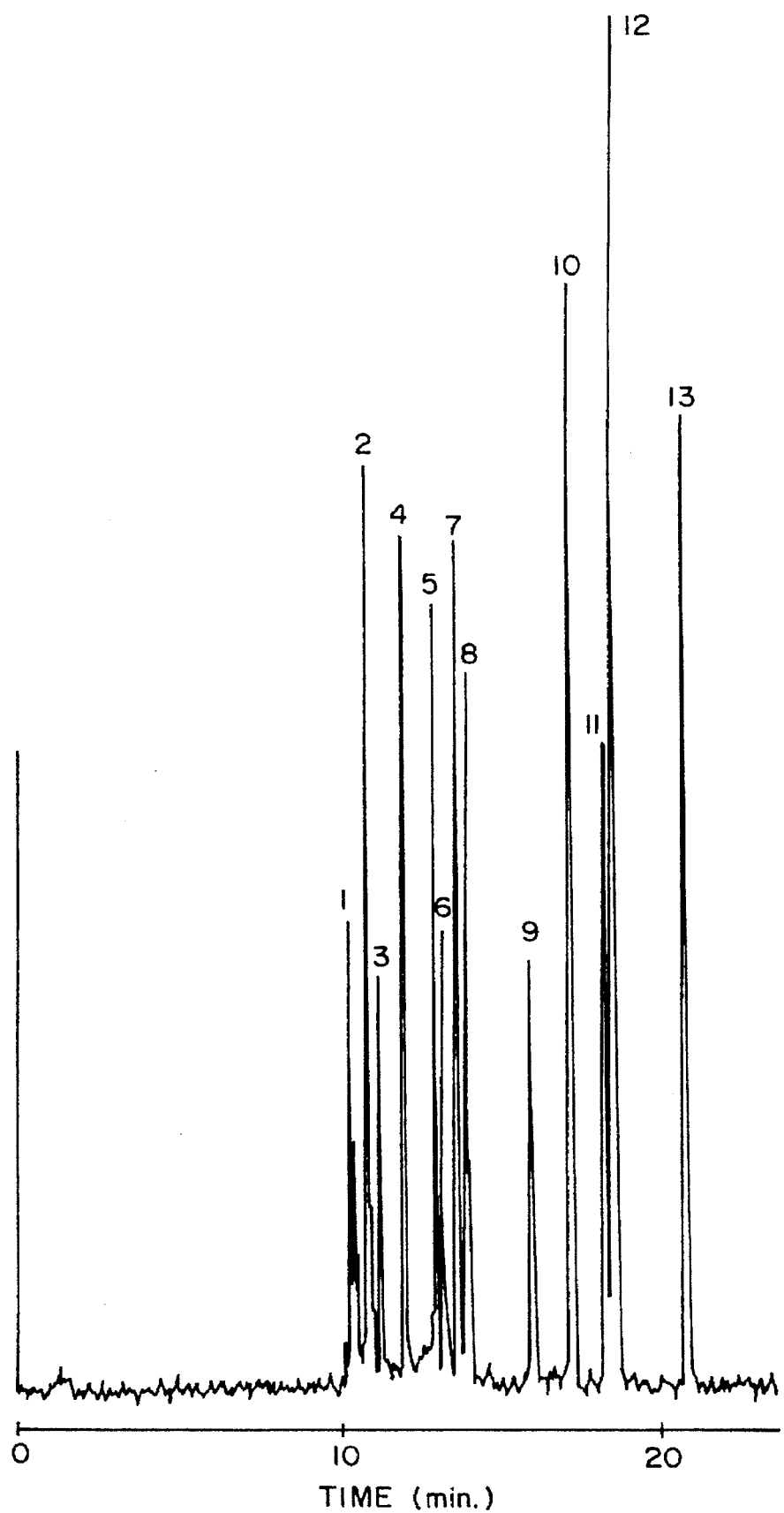

The use of highly sensitive laser detection underscores the resolving power and rapidity of capillary zone electrophoresis. Without buffer optimization efforts, large numbers of theoretical plates were readily achieved for mono- and and oligosaccharides. The values ranged from 100,000 to 400,000 theoretical plates per meter. FIG. 15B demonstrates separation of a 12-component monosaccharide mixture in about 20 minutes using borate as a buffer additive beneficial to separation. Complexation of hydroxy groups with borate ion, by magnifying small steric differences between closely related isomers, as shown in Example 3, FIG. 10 and 11, enhances resolution in addition to contributing to the charged character of these solutes.

EXAMPLE 5

Analysis of Glycoprotein Carbohydrates

In structural studies of glycoproteins, a high-sensitivity analysis of carbohydrate chains is fundamentally important. Effective isolation of glycans and their subsequent compositional analysis at high sensitivity has occupied researchers for some time; the substantial improvement of the present techniques over other techniques is demonstrated herein.

Figure 16B:
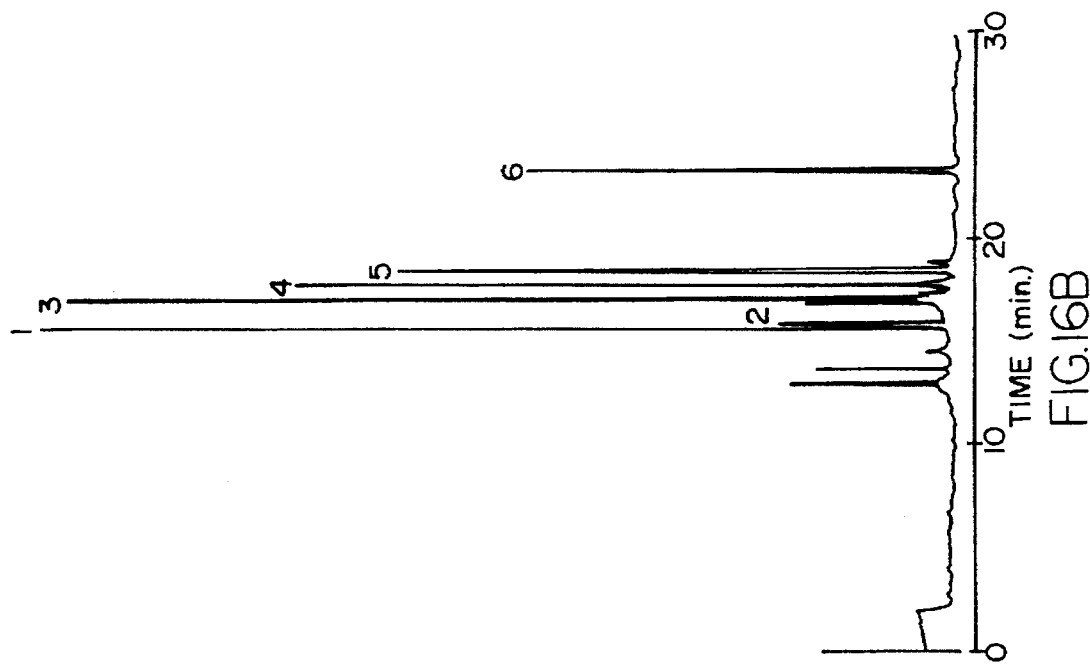
Figure 16A:
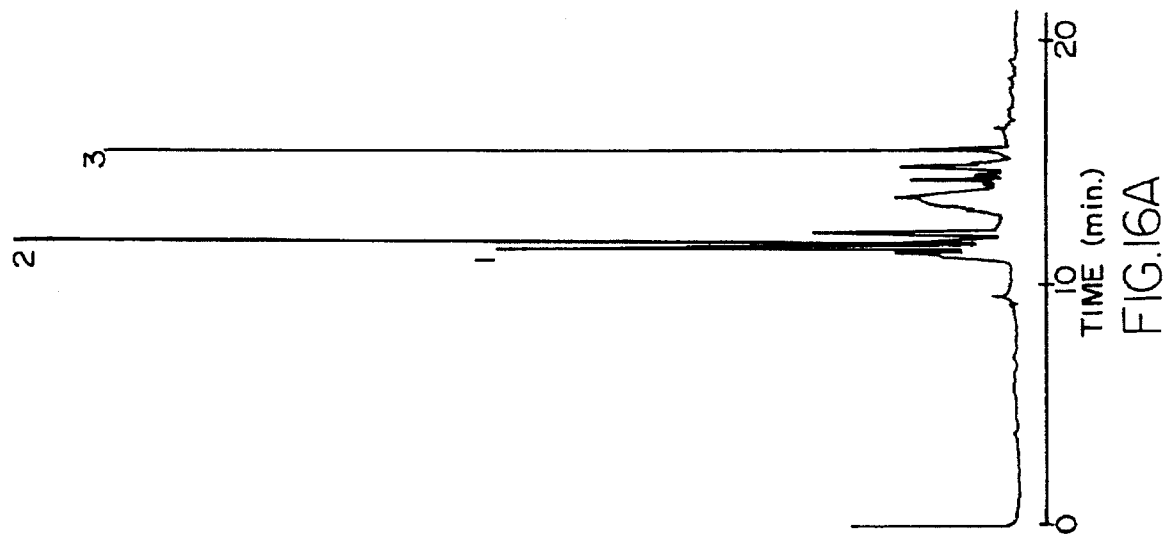
Figure 16D:
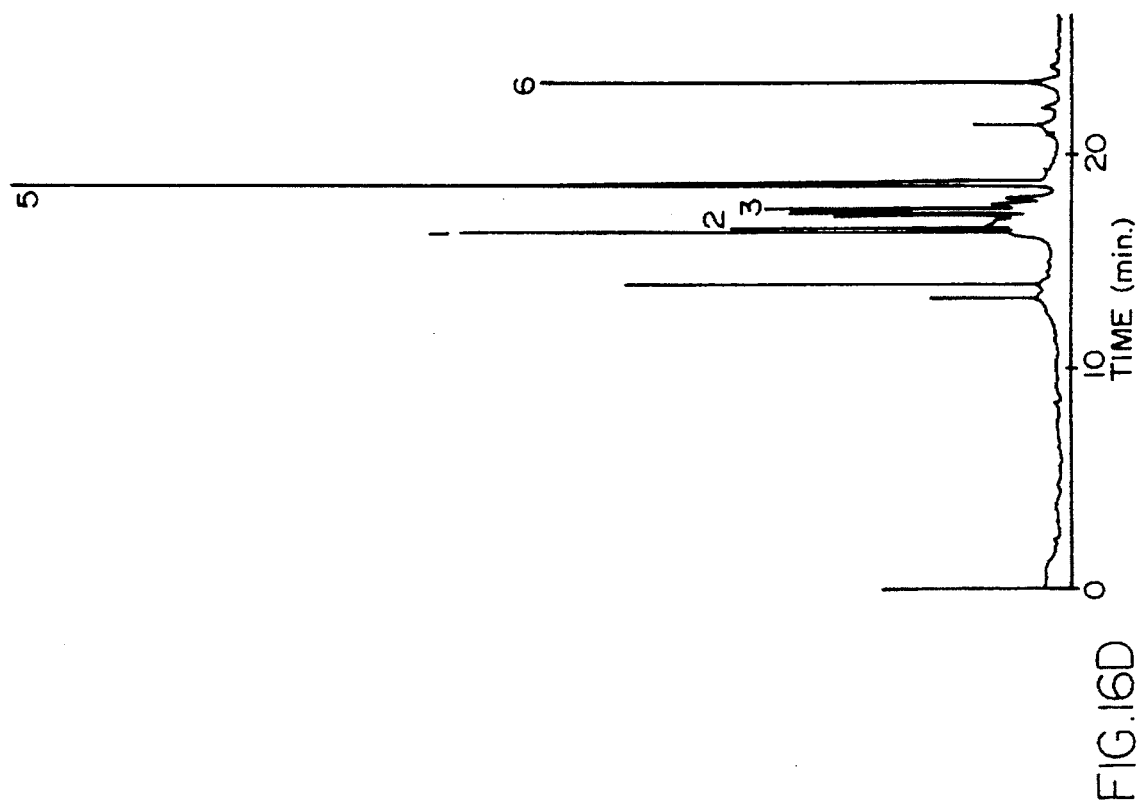
Figure 16C:
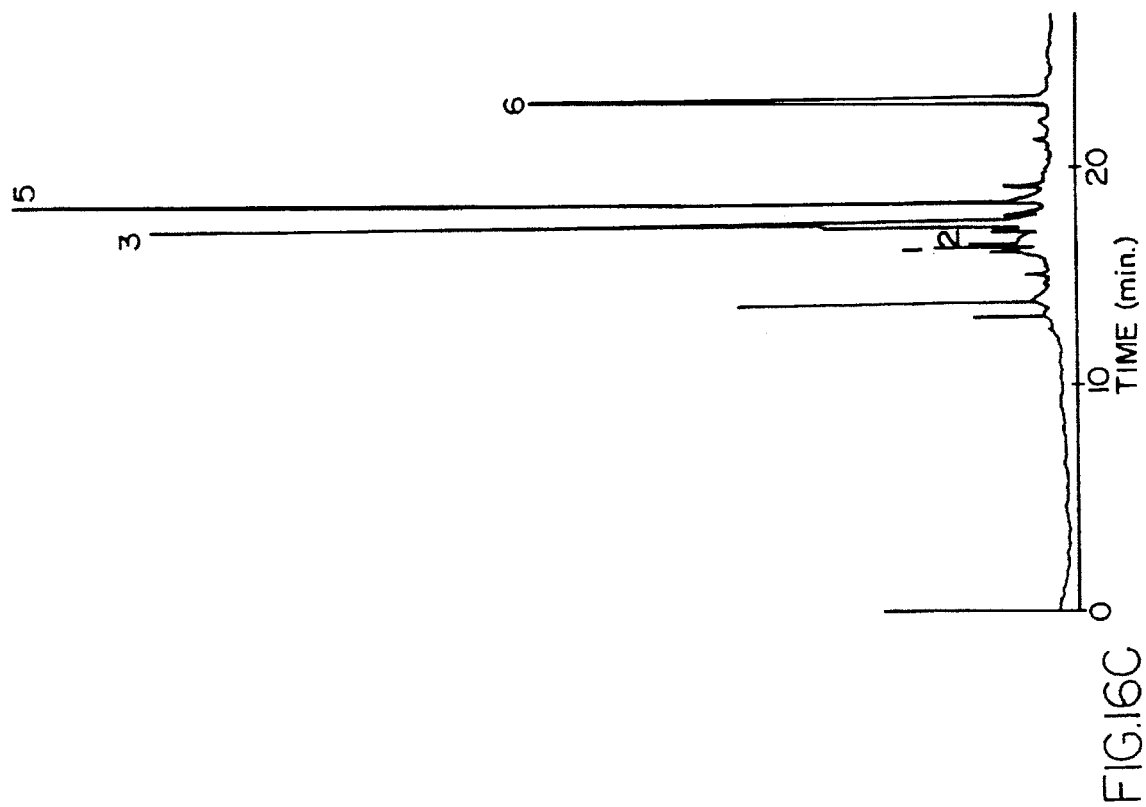

The most common glycoproteins contain two neutral sugars, mannose and galactose, and two amino sugar derivatives, N-acetylglucosamine and N-acetylgalactosamine. The neutral sugars can be easily released from a glycoprotein by hydrolysis with 2.0M trifluoroacetic acid in 6 hours at 100° C. For a complete release of hexosamines, stronger acidic conditions are needed. Usually, a glycoprotein is hydrolyzed by 4.0M hydrochloric acid for 6 hours at 100° C., generating the amino sugars completely from their N-acetylated derivatives. The resultant amino acids and peptides are removed from the mixture, and hexosamines are directly determined by fluorescent derivatization; non-amino sugars will not be derivatized. FIG. 16(A) shows the electropherogram obtained from a hydrolysate of bovine fetuin in 4.0M HCl. Under these conditions, the peaks for glucosamine and galactosamine were clearly indicated, while the third major peak likely corresponds to N-deacetylated sialic acid. An analysis of non-amino sugars necessitates reacetylation of endogeneous hexosamines after hydrolysis (to block their derivatization with the present XArQCA reagents), followed by reductive amination of non-amino sugars and derivatization with a fluorogenic reagent. The results obtained from this approach are also presented in FIG. 16 (B–D). The electropherogram of trifluoroacetic acid hydrolysate reveals the presence of neutral sugars mannose and galactose, and hexosamines [FIG. 16(C)], but two amino sugars do not seem to be well detected due to their incomplete release by trifluoroacetic acid. FIG. 16(D) shows the results from fetuin oligosaccharides hydrolyzed by hydrochloric acid, clearly giving the four major monosaccharide components (identified through standards).

Another exciting use of the present capillary electrophoresis/laser fluorescence system is in high-sensitivity oligosaccharide "mapping" (an analogy to peptide mapping in protein studies). Complex oligosaccharide mixtures are separated and detected following the isolation of glycan entities and their further fragmentation. Enzymes, such as glycopeptidase F (Townsend et al., 1989, Anal. Biochem. 182:1–8) and pronase (Hung et al., 1970, Carbohydr. Res. 13:127–137) can be used for releasing carbohydrates from polypeptide matrix. Hydrazinolysis also represents a simple means for releasing glycosides, giving as a major product free reducing oligosaccharides (Hase et al., 1984, J. Biochem. 95:197–203).

An electrophoretic oligosaccharide "map" obtained through hydrazinolysis of bovine fetuin demonstrates the feasibility of this approach (FIG. 17). The four major peaks most likely correspond to the oligosaccharides previously identified for fetuin (Townsend, et al., supra). Acquisition of standard compounds and mass-spectroscopic studies are needed to identify the various structural arrangements in these sugar molecules.

The injection volumes and the carbohydrate amounts introduced into the CE/laser fluorescence system described above correspond to subpicogram amounts of glycoproteins. Therefore the potential for detection of carbohydrates in extremely small samples (i.e. possibly, at the single-cell level) is clearly indicated.

EXAMPLE 6

Effects of Cyclodextrin on Fluorecence Intensity

The measured fluorescence intensity for CBQCA-tagged peptides increases significantly with an increasing concentration of cyclodextrin. The effects of α-cyclodextrin and β-cyclodextrin on the fluorescence intensity of a small peptide (Gly-Gly-Ayr-Arg) and a larger peptide (Des-Asp$^1$-angiotensin I) were compared. Relative fluorescence intensity of CBQCA-Des-Asp$^1$-Angiotensin I increased nearly 10 times with an increase of β-cyclodextrin concentration from 0 to 20 mM while a much smaller increase of fluorescence intensity was observed for CBQCA-Gly-Gly-Tyr-Arg. In contrast, α-cyclodextrin seems to favor small peptides for enhancement of fluorescence intensity. The cavity size of the cyclodextrins employed, as well as interactions between buffer additives and the peptides, appears to play a role.

The above preferred embodiments and examples are given to illustrate the scope and spirit of the present invention. These embodiments and examples will make apparent to those skilled in the art other embodiments and examples. These other embodiments and examples are within the contemplation of the present invention. Therefore, the present invention should be limited only by the appended claims.

What is claimed is:

1. A compound of the formula:

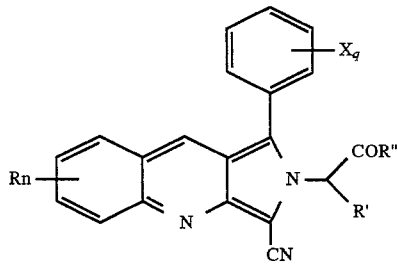

or salts thereof wherein

R is a lower alkyl,

X is an ionizable group, n is 0–5,

R' is a side chain of a naturally occurring amino acid,

R" is OH or (AA)$_w$, wherein AA is an amino acid moiety and w is an integer from 1–25, wherein said ionizable group is an alkyl carboxylic acid, an alkyl sulfonic acid, alkyl sulfinic acid, alkyl phosphonic acid, phenol, thiol, quaternary amine, amidinium, imide, beta-diketone or nitroalkane.

2. The compound of claim 1 wherein R is hydrogen.

3. The compound of claim 1 wherein the amino acid is a naturally occurring amino acid.

4. A compound of the formula:

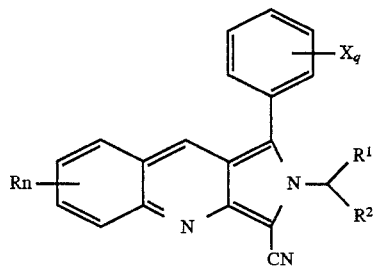

wherein

R is a lower alkyl,

X is an ionizable group, n is 1–5,

R'—CH—R$^2$ is a naturally occurring sugar, and said ionizable group is an alkyl carboxylic acid, an alkyl sulfonic acid, alkyl sulfinic acid, alkylphosphonic acid, phenol, thiol, quaternary amine, amidinium, imide, beta-diketone or nitroalkane.

5. The compound of claim 4 wherein the sugar is mannose, galactose, glucose, ribose, erythrose, talose or fucose.

6. The compound of claim 4 wherein R is hydrogen.

7. A product prepared by a process comprising reacting a primary amine with an XArQCA reagent in the presence of alkali cyanide, said XArQCA reagent having the formula:

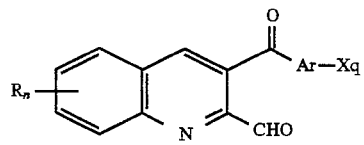

or salts thereof wherein

Ar is an aryl or heteroaromatic group;

One of R and X is an ionizable group and the other is hydrogen, lower alkyl, aryl, aryl lower alkyl, alkoxy, diloweralkylamine or piperidinyl group, and n and q are independently 0–5, provided at least one ionizable group is present, wherein said ionizable group is an alkyl carboxylic acid, an alkyl sulfonic acid, alkyl sulfinic acid, alkyl phosphonic acid, phenol, thiol, quaternary amine, amidinium, imide, beta-diketone or nitroalkane, said heteroaromatic group contains 5–14 ring atoms and 1, 2, or 3 ring heteroatoms selected from N, S or O, and, said primary amine is an alkylamine containing one to six carbon atoms, a naturally occurring amino acid, a peptide containing 2–50 naturally occurring amino acids, or an amino sugar.

8. The product of claim 7 wherein said primary amine is an amino sugar.

9. The product of claim 8 wherein said amino sugar is glucosamine, galactosamine, mannosamine, ribosamine, erythrosamine, talosamine, or furosamine.

10. The product of claim 7 wherein the ionizable group is —(CH$_2$)$_m$COOH, —(CH$_2$)$_m$OH, —(CH$_2$)$_m$SO$_3$H, —(CH$_2$)$_m$SO$_2$H, —(CH$_2$)$_m$SH, CH$_3$—(CH$_2$)$_m$—CO—N—(CH$_2$)$_{m1}$SO$_3$H,

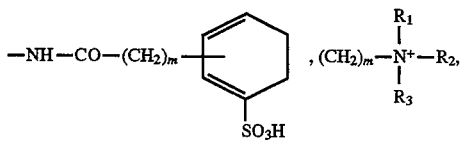

$-(CH_2)_m-CO-(CH_2)-CO-R_5$ or $-(CH_2)_z-NO_2$, wherein m and $m_1$ are independently 0–5, z is 1–5 and $R_1$, $R_2$, $R_3$ and $R_5$ are independently lower alkyl.

11. The compound of claim 1 wherein the ionizable group is $-(CH_2)_mCOOH$, $-(CH_2)_mOH$, $-(CH_2)mSO_3H$, $-(CH_2)_mSO_2H$, $-(CH_2)_mSH$, $CH_3-(CH_2)_m-CO-N-(CH_2)_{m1}SO_3H$,

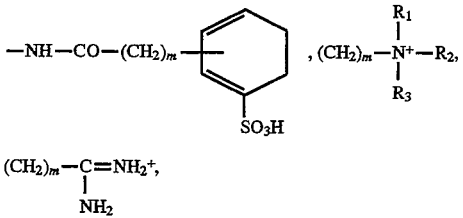

$-(CH_2)_m-CO-(CH_2)-CO-R_5$ or $-(CH_2)_z-NO_2$, wherein m and $m_1$ are independently 0–5, z is 1–5, and $R_1$, $R_2$, $R_3$ and $R_5$ are independently lower alkyl.

12. The compound of claim 4 wherein the ionizable group is $-(CH_2)_mCOOH$, $-(CH_2)_mOH$, $-(CH_2)mSO_3H$, $-(CH_2)_mSO_2H$, $-(CH_2)_mSH$, $CH_3-(CH_2)_m-CO-N-(CH_2)_{m1}SO_3H$,

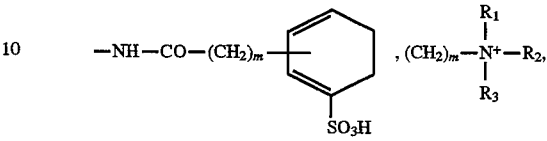

$-(CH_2)_m-CO-(CH_2)-CO-R_5$ or $-(CH_2)_z-NO_2$, wherein m and $m_1$ are independently 0–5, z is 1–5, and $R_1$, $R_2$, $R_3$, and $R_5$ are independently lower alkyl.

13. The product according to claim 7 wherein Ar is phenyl, naphthyl, furyl, thienyl, oxazolyl, pyrrolyl, pyridyl, imidazoyl or pyrimidyl.

14. The product according to claim 13 wherein Ar is phenyl or furyl.

15. The product according to claim 9 wherein the amino sugar is galactosamine.

* * * * *

UNITED STATES PATENT AND TRADEMARK OFFICE
CERTIFICATE OF CORRECTION

PATENT NO. : 5,631,374

DATED : May 20, 1997

INVENTOR(S) : Milos V. Novotny, et al.

Page 1 of 2

It is certified that error appears in the above-identified patent and that said Letters Patent is hereby corrected as shown below:

Column 1, line 7, insert the following: --This invention was made with Government support under Grant No. GM-24349-10 awarded by the National Institutes of Health. The Government has certain rights in the invention."--

Column 3, line 28: delete "(CBQCA) derivatized glycine"

Column 3, line 67: "B" should read --ß--

Column 5, line 35: after "least" insert --2--

Column 5, line 60: after "$CH_3$-" insert --$(CH_2)_m$ CO-N- --

Column 6, line 44: "(At)" should read --(Ar)--

Column 6, line 54: "m1" should read --$m_2$--

Column 8, line 35: "$X_q$" should read --$X_q$-Ar--

Column 10, line 62: delete "D"

Column 10, line 65: "on may" should read --on 7 may--

Column 12, line 56: "NH" should read --$NH_2$--

Column 14, line 7: "B" should read --ß--

Column 16, line 55: "4:230." should read --4:230).--

Column 18, line 24: "CaC12" should read --$CaCl_2$--

Column 19, line 26: "he" should read --the--

Column 20, line 21: "$\nu$ g/l" should read --$\nu$ g/$\mu$ l--

UNITED STATES PATENT AND TRADEMARK OFFICE
CERTIFICATE OF CORRECTION

PATENT NO. : 5,631,374
DATED : May 20, 1997
INVENTOR(S) : Milos V. Novotny, et al.

It is certified that error appears in the above-identified patent and that said Letters Patent is hereby corrected as shown below:

Column 22, line 2: insert --(CBQCA)--
Column 24, line 18: "mM-cyclodextrin" should read --mM $\alpha$-cyclodextrin--
Column 24, line 24: "a-" should read --a--
Column 25, line 55: "1131" should read --113)--
Column 26, line 65: "NH $_3$" should read --OH--

Signed and Sealed this

Twenty-fifth Day of August, 1998

Attest:

BRUCE LEHMAN

Attesting Officer

Commissioner of Patents and Trademarks